US006759513B2

(12) United States Patent
Yu et al.

(10) Patent No.: US 6,759,513 B2
(45) Date of Patent: *Jul. 6, 2004

(54) DEATH DOMAIN CONTAINING RECEPTORS

(75) Inventors: Guo-Liang Yu, Darnestown, MD (US); Jian Ni, Rockville, MD (US); Reiner L. Gentz, Silver Spring, MD (US); Patrick J. Dillon, Gaithersburg, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/333,966

(22) Filed: Jun. 16, 1999

(65) Prior Publication Data

US 2002/0009773 A1 Jan. 24, 2002

Related U.S. Application Data

(62) Division of application No. 08/815,469, filed on Mar. 11, 1997, now Pat. No. 6,153,402.
(60) Provisional application No. 60/013,285, filed on Mar. 12, 1996, provisional application No. 60/028,711, filed on Oct. 17, 1996, and provisional application No. 60/037,341, filed on Feb. 6, 1997.

(51) Int. Cl.[7] ............................................. C07K 14/705
(52) U.S. Cl. .......................................... 530/350; 514/2
(58) Field of Search .............................. 530/350; 514/2

(56) References Cited

U.S. PATENT DOCUMENTS

| 4,179,337 A | 12/1979 | Davis et al. ................. 435/181 |
| 5,120,525 A | 6/1992 | Goldenberg ................. 424/1.1 |
| 5,349,052 A | 9/1994 | Delgado et al. |
| 5,395,760 A | 3/1995 | Smith et al. ............. 435/240.1 |
| 5,464,938 A | 11/1995 | Smith et al. ................. 530/350 |
| 5,478,925 A | 12/1995 | Wallach et al. |
| 5,643,575 A | 7/1997 | Martinez et al. |
| 5,656,272 A | 8/1997 | Le et al. ................... 424/133.1 |

FOREIGN PATENT DOCUMENTS

| CA | 2260754 | 1/1998 |
| EP | 0 401 384 B1 | 12/1990 |
| EP | 0 506 477 B1 | 9/1992 |
| EP | 0 585 939 A2 | 3/1994 |
| WO | WO 98/06842 | 2/1988 |
| WO | WO 94/09137 | 4/1994 |
| WO | WO 94/13808 | 6/1994 |
| WO | WO 95/06058 | 3/1995 |
| WO | WO 95/10540 | 4/1995 |
| WO | WO 96/14328 | 5/1996 |
| WO | WO 96/26736 | 9/1996 |
| WO | WO 96/34095 | 10/1996 |
| WO | WO 96/39515 | 12/1996 |
| WO | WO 97/33899 | 9/1997 |
| WO | WO 97/33904 | 9/1997 |
| WO | WO 97/34911 | 9/1997 |
| WO | WO 97/37020 | 10/1997 |
| WO | WO 98/02543 | 1/1998 |
| WO | WO 98/07832 | 2/1998 |
| WO | WO 98/07880 | 2/1998 |
| WO | WO 98/14565 | 4/1998 |
| WO | WO 98/18921 | 5/1998 |
| WO | WO 98/30693 | 7/1998 |
| WO | WO 98/30694 | 7/1998 |
| WO | WO 98/32466 | 7/1998 |
| WO | WO 98/32856 | 7/1998 |
| WO | WO 98/41629 | 9/1998 |
| WO | WO 98/49305 | 11/1998 |
| WO | WO 98/56892 | 12/1998 |
| WO | WO 00/08139 | 2/2000 |

OTHER PUBLICATIONS

Chen, G., et al., "Induction of p53–Independent Apoptosis by Hygromycin B: Suppression by Bcl–2 and Adenovirus E1B 19—kDa Protein," *Exp. Cell Res. 221*:55–59, Academic Press, Inc. (Nov. 1995).

Cotter, T.G., et al., "The Induction of Apoptosis by Chemotherapeutic Agents Occurs in All Phases of the Cell Cycle," *Anticancer Res. 12*:773–780, J.G. Delinassios (1992).

Huss, R., et al., "Cyclosporine–induced apoptosis in CD4' T lymphocytes and computer–simulated analysis: modeling a treatment scenario for HIV infection," *Res. Immunol. 146:*101–108, Elsevier (Feb. 1995).

Van Antwerp, D.J., et al., "Inhibition of TNF–induced apoptosis by NF–KB," *Trends Cell Biol. 8:*107–111, Elsevier Science Ltd. (1998).

Walter, D.H., et al., "Cyclosporin A Inhibits Apoptosis of Human Endothelial Cells by Preventing Release of Cytochrome C From Mitochondria," *Circulation 98:*1153–1157, American Heart Association, Inc. (1998).

Wang, E.C.Y., et al., "DR3 Regulates Negative Selection during Thymocyte Development," *Mol. Cell. Biol. 21:*3451–3461, American Society for Microbiology (2001).

Arend, W.P. et al., "Binding of IL–1α, IL–1β, and IL–1 Receptor Antagonist by Soluble IL–1 Receptors and Levels of Soluble IL–1 Receptors in Synovial Fluids," J. Immunol. 153:4766–4774 (1994).

(List continued on next page.)

*Primary Examiner*—John D. Ulm
(74) *Attorney, Agent, or Firm*—Human Genome Sciences, Inc.

(57) ABSTRACT

The present invention relates to novel Death Domain Containing Receptor (DR3 and DR3-V1) proteins which are members of the tumor necrosis factor (TNF) receptor family. In particular, isolated nucleic acid molecules are provided encoding the human DR3 and DR3-V1 proteins. DR3 and DR3-V1 polypeptides are also provided, as are vectors, host cells and recombinant methods for producing the same. The invention further relates to screening methods for identifying agonists and antagonists of DR3 and DR3-V1 activity.

16 Claims, 10 Drawing Sheets

OTHER PUBLICATIONS

Ashkenazi, A. et al., "Protection against endotoxic shock by a tumor necrosis factor receptor immunoadhesin," *Proc. Natl. Acad. Sci. USA* 88:10535–10539 (1991).

Beutler, B. and Cerami, A., "Tumor Necrosis, Cachexia, Shock, and Inflammation: A Common Mediator," *Ann. Rev. Biochem.* 57:505–518 (1988).

Boldin, M.P. et al., "A Novel Protein That Interacts with the Death Domain of Fas/APO1 Contains a Sequence Motif Related to the Death Domain," *J. Biol. Chem.* 270:7795–7798 (Apr. 1995).

Boldin, M.P. et al., "Involvement of MACH, a Novel MORT1/FADD–Interacting Protease, in Fas/APO–1– and TNF Receptor–Induced Cell Death," *Cell* 85:803–815 (Jun. 1996).

Caliceti, P. et al., "Biopharmaceutical Properties of Uricase Conjugated to Neutral and Amphiphilic Polymers," *Bioconjugate Chem.* 10:638–646 (Aug. 1999).

Chinnaiyan, A.M. et al., "FADD, a Novel Death Domain–Containing Protein, Interacts with the Death Domain of Fas and Initiates Apoptosis," *Cell* 81:505–512 (May 1995).

Chinnaiyan, A.M. et al., "FADD/MORT1 Is a Common Mediator of CD95 (Fas/APO–1) and Tumor Necrosis Factor Receptor–induced Apoptosis," *J. Biol. Chem.* 271:4961–4965 (Mar. 1996).

Corti, A. et al., "Identification of an Epitope of Tumor Necrosis Factor (TNF)–Receptor Type 1 (p55) Recognized by a TNF–α–Antagonist Monoclonal Antibody," *Lymphokine Cytokine Res.* 13:183–190 (Jun. 1994).

Delgado, C. et al., "The Uses and Properties of PEG–Linked Proteins," *Crit. Rev. Ther. Drug Carrier Systems* 9:249–304 (1992).

Deng, B. et al., "An Agonist Murine Monoclonal Antibody to the Human c–Mpl Receptor Stimulates Megakaryocytopoiesis," *Blood* 92:1981–1988 (Sep. 1998).

Fiers, W. "Tumor necrosis factor," *FEBS Lett.* 285:199–212 (1991).

Francis, G.E. et al., "PEGylation of cytokines and other therapeutic proteins and peptides: the importance of biological optimisation of coupling techniques," *Intl. J. Hematol.* 68:1–18 (Jul. 1998).

Fu, M.L.X. et al., "Characterization of anti–peptide antibodies directed against an extracellular immunogenic epitope on the human $α_1$–adrenergic receptor," *Clin. Exp. Immunol.* 97:146–151 (Jul. 1994).

Goeddel, D.V. et al., "Tumor Necrosis Factor: Gene Structure and Biological Activities," *Cold Spring Harbor Symp. Quant. Biol. LI*:597–609 (1986).

Hahne, M. et al., "APRIL, a New Ligand of the Tumor Necrosis Factor Family Stimulates Tumor Cell Growth," *J. Exp. Med.* 188:1185–1190 (Sep. 1998).

Hsu, H. et al., "The TNF Receptor 1–Associtated Protein TRADD Signals Cell Death and NF–$_k$B Activation," *Cell* 81:495–504 (May 1995).

Hsu, H. et al., "TRADD–TRAF2 and TRADD–FADD Interactions Define Two Distinct TNF Receptor 1 Signal Transduction Pathways," *Cell* 84:299–308 (Jan. 1996).

Hsu, H. et al., "TNF–Dependent Recruitment of the Protein Kinase RIP to the TNF Receptor–1 Signaling Complex," *Immunity* 4:387–396 (Apr. 1996).

Hughes, D.P.M. and Crispe, I.N. "A Naturally Occurring Soluble Isoform of Murine Fas Generated by Alternative Splicing," *J. Exp. Med.* 182:1395–1401 (Nov. 1995).

Kischkel, F.C. et al., "Cytotoxicity–dependent APO–1 (Fas/CD95)–associated proteins form a death–inducing signaling complex (DISC) with the receptor," *EMBO J.* 14:5579–5588 (Nov. 1995).

Malik, F. et al., "Polyethylene Glycol (PEG)–modified Granulocyte–Macrophage Colony–stimulating Factor (GM–CSF) with Conserved Biological Activity," *Exp. Hematol.* 20:1028–1035 (1992).

Morpurgo, M. et al., "Covalent Modification of Mushroom Tyrosinase with Different Amphiphic Polymers for Pharmaceutical and Biocatalysis Applications," *App. Biochem. Biotech.* 56:59–72 (Jan. 1996).

Old, L.J. "Tumor Necrosis Factor," *Scientific American* 258:59–75 (1988).

Rothe, M. et al. "TRAF2–Mediated Activation of NF–$_k$B by TNF Receptor 2 and CD40," *Science* 269:1424–1427 (Sep. 1995).

Stanger, B.Z. et al. "RIP: A Novel Protein Containing a Death Domain That Interacts with Fas/APO–1 (CD95) in Yeast and Causes Cell Death," *Cell* 81:513–23 (May 1995).

Tartaglia, L. A. et al., "Tumor Necrosis Factor's Cytotoxic Activity is Signaled by the p55 TNF Receptor," *Cell* 73:213–216 (1993).

Tewari, M. and Dixit, V.M, "Fas– and Tumor Necrosis Factor–induced Apoptosis Is Inhibited by the Poxvirus crmA Gene Product," *J. Biol. Chem.* 270:3255–3260 (Feb. 1995).

Vorobjev, P. E. et al., "Oligonucleotide Conjugated to Linear and Branched High Molecular Weight Polyethylene Glycol as Substrates for RNase H.," *Nucleosides & Nucleotides* 18:2745–2750 (Nov.–Dec. 1999).

Yoon, S.T. et al., "Both High and Low Avidity Antibodies to the T Cell Receptor Can Have Agonist or Antagonist Activity," *Immunity* 1:563–569 (Oct. 1994).

Adams, M.D. et al., "Complementary DNA Sequencing: Expressed Sequence Tags and Human Genome Project," *Science* 252:1651–1656 (1991).

Adams, M.D. et al., "Sequence identification of 2,375 human brain genes," *Nature* 355:632–634 (1992).

Aggarwal, B.B. and K. Natarjan, "Tumor necrosis factors: Developments during the last decade," *Eur. Cytokine Netw.* :93–124 (Apr.–Jun. 1996).

Altschul, S.F. et el., "Basic Local Alignment Search Tool," *J. Mol. Biol.* 215:403–410 (1990).

Ansari, A.A. et al., "HLA–D gene studies in relation to immune responsiveness to a grass allergen LoI P III," *Immunogenet.* 33:24–32 (1991).

Armitage, R.J., "Tumor necrosis factor receptor superfamily members and their ligands," *Curr. Opin. Immunol* 6:407–413 (Jun. 1994).

Baens, M. et al., "Construction and Evaluation of a hncDNA Library of Human 12p Transcribed Sequences Derived from a Somatic Cell Hybrid," *Genomics* 16:214–218 (1993).

Baker, E. et al., "Chromosomal location of the human tumor necrosis factor receptor genes," *Cytogenet. Cell Genet.* 57:117–118 (1991).

Banchereau, J. et al., "Long–Term Human B Cell Lines Dependent on Interleukin–4 and Antibody to CD40," *Science* 251:70–72 (1991).

Banner, D.W. et al., "Crystal Structure of the Soluble Human 55 kd Receptor–Human TNFB Complex: Implications for TNF Receptor Activation," *Cell* 73:431–445 (1993).

Baum, P.R. et al., "Molecular characterization of murine and human OX40/OX40 ligand systems: identification of a human OX40 ligand as the HTLV-1-regulated protein gp34," *EMBO J.* 13(17):3992–4001 (Sep. 1994).

Birkeland, M.L. et al., "Gene structure and chromosomal localization of the mouse homologue of rat OX40 protein," *Eur. J. Immunol* 5:926–930 (Apr. 1995).

Bodmer, J.–L, et al.; "TRAMP, a Novel Apoptosis–Mediating Receptor with Sequence Homology to Tumor Necrosis Factor Receptor 1 and Fas(Apo–1/CD95)," *Immunity* 6:79–88 (Jan. 1997).

Camerini, D. et al., "The T Cell Activation Antigen CD27 Is a Member of the Nerve Growth Factor/Tumor Necrosis Factor Receptor Gene Family," *J. Immunol.* 147(9):3165–3169 (1991).

Chinnaiyan, A.M. et al., "Signal Transduction by DR3, a Death Domain–Containing Receptor Related to TNFR–1 and CD95," *Science* 274:990–992 (Nov. 1996).

Dürkop, H. et al., "Molecular Cloning and Expression of a New Member of the Nerve Growth Factor Receptor Family That Is Characteristic for Hodgkin's Disease," *Cell* 68:421–427 (1992).

Engelmann, H. et al , "Two Tumor Necrosis Factor–binding Proteins Purified from Human Urine," *J. Biol. Chem.* 265(3):1531–1536 (1990).

Feinstein, E. et al., "The death domain: a module shared by proteins with diverse cellular functions," *TIBS* 20:342–344 (Sep. 1995).

Gillette–Ferguson, I. and C.L. Sidman, "A specific intercellular pathway of apoptotic cell death is defective in the mature peripheral T cells of autoimmune lpr and gld mice," *Eur. J. Immunol.* 24:1181–1185 (May 1994).

Goodwin, R.G. et al., "Molecular cloning of a ligand for the inducible T cell gene 4–1BB: a member of an emerging family of cytokines with homology to tumor necrosis factor," *Eur. J. Immunol.* 23:2631–2641 (1993).

Gruss, H.–J et al., "Pleiotropic Effects of the CD30 Ligand on CD30–Expressing Cells and Lymphoma Cell Lines," *Bio* :2045–2056 (Apr. 1994).

Himmler, A. et al., "Molecular Cloning and Expression of Human and Rat Tumor Necrosis Factor Receptor Chain (p60) and Its Soluble Derivative, Tumor Necrosis Factor–Binding Protein," *DNA and Cell Biol.* 9(10):705–715 (1990).

Hohmann, H.–P. et al., "Two Different Cell Types Have Different Major Receptors for Human Tumor Necrosis Factor (TNF.,)," *J. Biol. Chem.* 264(25):14927–14934 (1989).

Howard, S.T. et al., "Vaccinia Virus Homologues of the Shope Fibroma Virus Inverted Terminal Repeat Proteins and a Discontinuous ORF Related to the Tumor Necrosis Factor Receptor Family," *Virol.* 180:633–647 (1991).

Hsu, K.C. and M.V. Chao, "Differential Expression and Ligand Binding Properties of Tumor Necrosis Factor Receptor Chimeric Mutants," *J. Biol. Chem.* 268(22)16430–16436 (1993).

Hu, F.–Q. et al., "Cowpox Virus Contains Two Copies of an Early Gene Encoding a Soluble Secreted Form of the Type II TNF Receptor," *Virol.* 204:343–356 (Oct. 1994).

Inui, S. et al., "Idenfication of the intracytoplasmic region essential for signal transduction through a B cell activation molecule, CD40," *Eur. J. Immunol.* 20:1747–1753 (1990).

Itoh, N. et al., "The Polypeptide Encoded by the cDNA for Human Cell Surface Antigen Fas Can Mediate Apoptosis," *Cell* 66:233–243 (1991).

Johnson, D. et al., "Expression and Structure of the Human NGF Receptor," *Cell* 47:545–554 (1986).

Kitson, J. et al., "A death–domain–comtaining receptor that mediates apoptosis," *Nature* 384:372–375 (Nov. 1996).

Krammer, P.H. et al., "Regulation of apoptosis in the immune system," *Curr. Opin. Immunol.* 6:279–289 (Apr. 1994).

Kwon, B.S. and S.M. Weissman, "cDNA sequences of two inducible T–cell genes," *Proc. Natl. Acad. Sci. USA* 86:1963–1967 (1989).

Kwon, B.S. et al., "Genomic Organization and Chromosomal Localization of the T–Cell Antigen 4–1BB," *J. Immunol.* 152:2256–2262 (Mar. 1994).

Lewis, M. et al., "Cloning and expression of cDNAs for two distinct murine tumor necrosis factor receptors demonstrate one receptor is species," *Proc. Natl. Acad. Sci. USA* 88:2830–2834 (1991).

Loetscher, H. et al., "Molecular Cloning and Expression of the Human 55 kd Tumor Necrosis Factor Receptor," *Cell* 61:351–359 (1990).

Mallett, S. et al., "Characterization of the MRC OX40 antigen of activated CD4 positive T lymphocytes—a molecule related to nerve growth factor receptor," *EMBO J.* 914):1063–1068 (1990).

Mallett, S. and A.N. Barclay, "A new superfamily fo cell proteins related to the nerve growth factor receptor," *Immunol. Today* 12(7):220–223 (1991).

Marster, S. et al., "Apo–3, a new member of the tumor necrosis factor receptor family, contains a death domain and activates apoptosis and NF-$_k$B," *Current Biology* 6:1669–1676 (Dec. 1996).

Montgomery, R. I. et al., "A New Member of the TNG–NGF Receptor Family Can Mediate Herpes Simplex Virus 1 Into Cells," *Eur. Cytokine Netw.* 712):159, Abstract No. L7 (1996).

Muzio, M. et al., "FLICE, A Novel FADD–Homologous ICE/CED–3–like Protease, Is Recruited to the CD95 (FAS/APO–1) Death–Inducing Signaling Complex," *Cell* 85:817–827 (Jun. 1996).

Nakagawa, T. et al., "Identification of an isoform with an extremely large Cys–rich region of PC6, a Kex2–like processing endoprotease," *FEBS Letter* 327:165–171 (1993).

Nophar, Y. et al., "Soluble forms of tumor necrosis factor receptors (TNF–Rs). The cDNA for the type 1 TNF–R, cloned using amino acid sequence data of its soluble form, encodes both the celi surface and a soluble form of the receptor," *EMBO J.* :3269–3278 (1990).

Pfeffer, K. et al., "Mice Deficient for the 55 kd Tumor Necrosis Factor Receptor Are Resistant to Endotoxic Shock, yet Succumb to L. Monotyogenes Infections," *Cell* 73:457–467 (1993).

Piguet, P.F. et al., "Evolution of collagen arthritis in mice is arrested by treatment with anti–tumor necrosis factor (TNF) antibody or a recombinant soluble TNF receptor," *Immunol* 77:510–514 (1992).

Pollok, K.E. et al., "Inducible T Cell Antigen 4–1BB," *J Immunol* 150(3):771–781 (1993).

Radeke, J.J. et al., "Gene transfer and molecular cloning of the rat nerve growth factor receptor," *Nature* 325:593–597 (1987).

Roitt, I. et al., *Immunology,* 3rd Ed., Mosby, St. Louis, MO, pp. 4.16–4.17 (1994).

Rossol–Voth, R. et al., "In vivo protective effect of tumor necrosis factor against experimental infection with herpes simplex virus type 1," *J Ser. Virol.* :143–147 (1991).

Rothe, M. et al., "A Novel Family of Putative Signal Transducers Associated with the Cytoplasmic Domain of the 75 kDa Tumor Necrosis Factor Receptor," *Cell 78:*681–692 (Aug. 1994).

Schall, T.J. et al., "Moleucular Cloning and Expression of a Receptor for Human Tumor Necrosis Factor," *Cell 61:*361–370 (1990).

Screaton, G. et al., "LARD: A new lymphoid–specific death domain containing receptor regulated by alternative pre–mRNA splicing," *Proc. Natl. Acad. Sci. USA 94:*4615–4619 (1997).

Smith, C.A. et al., "A Receptor for Tumor Necrosis Factor Defines as Unusual Family of Cellular and Viral Proteins," *Science 248:*1019–1023 (1990).

Smith, C.A. et al., "T2 Open Reading Frame from the Shope Fibroma Virus Encodes a Soluble Form of the TNF Receptor," *Biochem.Biophys Res. Comm 176(1)*:335–342 (1991).

Smith, C.A. et al., "CD30 Antigen, a Marker for Hodgkin's Lymphoma, Is a Receptor Whose Ligand Defines an Emerging Family of Cytokines with Homology to TNF," *Cell 73:*1349–1360 (1993).

Smith, G.L., "Vaccinia virus glycoproteins and immune evasion," *J. Gen. Virol. 74:*1725–1740 (1993).

Stamenkovic, I. et al., "A B–Lymphocyte activation molecule related to the nerve growth factor receptor and induced by cytokines in carcinomas," *EMBO J. 8(5)*:1403–1410 (1989).

Tartaglia, L.A. et al., "The two different receptors for receptors for tumor necrosis factor mediate distinct cellular responses," *Natl. Acad. Sci. USA 88:*9292–9296 (1991).

Tartaglia, L.A. and D.V. Goeddel, "Tumor Necrosis Factor Receptor Signaling," *J. Biol. Chem. 267(7):*4304–4307 (1992).

Tartaglia, L.A. et al., "A Novel Domain within the 55 kd TNF Receptor Signals Cell Death," *Cell 74:*845–853 (1993).

Torcia, M. et al., "Nerve Growth Factor Is an Autocrine Survival Factor for Memory B Lymphocytes," *Cell 66:*345–356 (1996).

Van Lier, R.A.W. et al., "Tissue Distribution and Biochemical and Functional Properties of Tp55 (CD27), a Novel T Cell Differentiation Antigen," *J. Immunol. 139(5)*:1589–1596 (1987).

Van Ostade, X. et al., "Human tumor necrosis factor mutants with preferential binding to and activity on either the R55 or R75 receptor," *Eur. J. Biochem. 226:*771–779 (Mar. 1994).

Vandenbeele, P. et al., "Two tumor necrosis factor receptors: structure and function," *Trends Cell. Biol. 5:*392–399 (Oct. 1995).

Database Embl–new3 on MASPAR, Acc. No. L23876, Glascow, E. and Schechter, N., "Nucleotide sequence of a GFAP–like Intermediate Filament cDNA from Goldfish retina," submitted Sep. 1, 1993.

Database EST–STS on MASPAR, (St. Louis, MO, USA), Acc. No. H14106, Hiller, L. et al., "WashU–Merck EST Project," submitted Jul. 10, 1995.

Database EMBL/GenBank/DDJB on MASPAR, Genetique Molelculaire (sic) et Biologie du development (Villejuif Cedex, France), Acc. No. Z38433, GENEXPRESS, Direct Submitted Oct. 26, 1994.

Database EST–STS on MASPAR, Whitehead Institute/MIT Center for Genome Research (Cambridge, MA, USA), Acc. NO. G11923, Hudson, T., "Whitehead Institute/MIT Center for Genome Research; Physically Mapped ST5s," submitted Oct. 23, 1995.

Database EMBL–new3 on MASPAR, Acc. No. X60370, X60371, X60550, Zauner, W. et al., "Identification of Two Distinct microtubule Binding Domains on Recombinant Rat MAP 1B," submitted Oct. 21, 1992.

Database EMBL–new3 on MASPAR, Acc. No. X75491, Aslanidis, C. et al., "Genomic Organization of the Human Lysosmal Acid Lipase Gene (LIPA)," Submitted Mar. 1, 1994.

Database A–Geneseq24 on MASPAR, Acc. No. R38859, Aruffo, A.A. et al., "CD40CR Receptor and its' (sic) Ligands used to Inhibit B–Cell Activation in Allergy and Auto–immune Disease," submitted Feb. 7, 1994, EP, A, 555880, Aug. 18, 1993.

EST–STS Database on MASPAR, The WashU–Merck EST Project, Accession No. H46211 (Jul. 1995).

EST–STS Database on MASPAR, The WashU–Merck EST Project, Accession No. H46374 (Jul. 1995).

EST–STS Database on MASPAR, The WashU–Merck Est Project, Accession No. H41851 (Jul. 1995).

EST–STS Database on MASPAR, The WashU–Merck EST Project, Accession No. H46662 (Jul. 1995).

EST–STS Database on MASPAR, The WashU–Merck EST Project, Accession No. H49675 (Jul. 1995).

EST–STS Database on MASPAR, The WashU–Merck EST Project, Accession No. H46378 (Jul. 1995).

EST–STS Database on MASPAR, The WashU–Merck EST Project, Accession No. H46424 (Jul. 1995).

NBI Entrez, GenBank Report, Accession No. H19739, from Hillier, L. et al. (Jul. 1995).

NCBI Entrez, GenBank Report, Accession No. H22502, from Hillier, L. et al (Jul. 1995).

NCBI Entrez, GenBank Report, Accession No. H41522, from Hillier, L. et al. (Jul. 1995).

NCBI Entrez, GenBank Report, Accession No. N63660, from Hillier, L. et al. (Mar. 1996).

NCBI Entrez, GenBank Report, Accession No. N71143, from Hillier, L. et al. (Mar. 1996).

NCBI Entrez, GenBank Report, Accession No. N71141, from Hillier, L. et al (Mar. 1996).

NCBI Entrez, GenBank Report, Accession No. W01590, from Hillier, L. et al., (Apr. 1996).

NCBI Entrez, GenBank Report, Accession No. W01592, from Hillier, L. et al., (Apr. 1996).

NCBI Entrez, GenBank Report, Accession No. W71984, from Hillier, L. et al., (Oct. 1996).

NCBI Entrez, GenBank Report, Accession No. W76376, from Hillier, L. et al., (Oct. 1996).

NCBI Entrez, GenBank Report, Accession No. AA088350, from Hillier, L. et al., (Oct. 1996).

NCBI Entrez, GenBank Report, Accession No. AA476747, from Hillier, L. et al. (Aug. 1997).

NCBI Entrez, GenBank Report, Accession No. AA476749, from Hillier, L. et al. (Aug. 1997).

NCBI Entrez, GenBank Report, Accession No. AA524052, from NCI–CGAP (Aug. 1997).

NCBI Entrez, GenBank Report, Accession No. AA088232, from Hillier, L. et al., (Oct. 1996).

NCBI Entrez, GenBank Report, Accession No. AA631757, from NCI–CGAP (Oct. 1997).

NCBI Entrez, GenBank Report, Accession No. AA709231, from NCI–CGAP (Jan. 1998).

NCBI Entrez, GenBank Report, Accession No. CAA70561, Kitson, J. et al. (Dec. 1996).

NCBI Entrez, GenBank Report, Accession No. AAB41432, Chaudhary, P.M. and Hood, L.E. (Jan. 1997).

NCBI Entrez, GenBank Report, Accession No. U94503, Screaton, G.R. et al. (May 1997).

NCBI Entrez, GenBank Report, Accession No. U94502, Screaton, G.R. et al. (May 1997).

NCBI Entrez, GenBank Report, Accession No. Y09392, Kitson, J. et al (Dec. 1996).

NCBI Entrez, GenBank Report, Accession No. U94509, Screaton, G.R. et al. (May 1997).

NCBI Entrez, GenBank Report, Accession No. U94510, Screaton, G.R. et al (May 1997).

NCBI Entrez, GenBank Report, Accession No. AAC51314, Screaton, G.R. et al. (Feb. 1999).

NCBI Entrez, GenBank Report, Accession No. AAC51192, Bodmer, J.L. et al. (Feb. 1999).

NCBI Entrez, GenBank Report, Accession No. NP 003781, Marsters, S.A. et al. (Mar. 1999).

```
          10                    30                    50
CATGGGTGGGGGTGGGGGCGCTGCTGGATTCCTGCTCTGGTGGAGGGGAAACTTGTGAGG 70                    90                    110
GGCTGGTAAGCGCCCCCTCCGAAGCCTGGTGTGTGCGCGGGGGGAAGGAAGTTAGTTTCC 130                   150                   170
TCTCCACCCATGGGCACCCCTTCTGCCCGGGGCCTGGGAAGTGGGCTGCTCTGTGGGCAA 190                   210                   230
ATGCTGGGGCCTCTGAAATGGAGGAGACGCAGCAGGGAGAGGCCCCACGTGGGCAGCTGC
                  M  E  E  T  Q  Q  G  E  A  P  R  G  Q  L  R 250                   270                   290
GCGGAGAGTCAGCAGCACCTGTCCCCCAGGCGCTCCTCCTGGTGCTGCTGGGGGCCCGGG
 G  E  S  A  A  P  V  P  Q  A  L  L  L  V  L  L  G  A  R  A 310                   330                   350
CCCAGGGCGGCACTCGTAGCCCCAGGTGTGACTGTGCCGGTGACTTCCACAAGAAGATTG
  Q  G  G  T  R  S  P  R  C  D  C  A  G  D  F  H  K  K  I  G 370                   390                   410
GTCTGTTTTGTTGCAGAGGCTGCCCAGCGGGGCACTACCTGAAGGCCCCTTGCACGGAGC
   L  F  C  C  R  G  C  P  A  G  H  Y  L  K  A  P  C  T  E  P 430                   450                   470
CCTGCGGCAACTCCACCTGCCTTGTGTGTCCCCAAGACACCTTCTTGGCCTGGGAGAACC
   C  G  N  S  T  C  L  V  C  P  Q  D  T  F  L  A  W  E  N  H 490                   510                   530
ACCATAATTCTGAATGTGCCCGCTGCCAGGCCTGTGATGAGCAGGCCTCCCAGGTGGCGC
   H  N  S  E  C  A  R  C  Q  A  C  D  E  Q  A  S  Q  V  A  L 550                   570                   590
TGGAGAACTGTTCAGCAGTGGCCGACACCCGCTGTGGCTGTAAGCCAGGCTGGTTTGTGG
   E  N  C  S  A  V  A  D  T  R  C  G  C  K  P  G  W  F  V  E 610                   630                   650
AGTGCCAGGTCAGCCAATGTGTCAGCAGTTCACCCTTCTACTGCCAACCATGCCTAGACT
   C  Q  V  S  Q  C  V  S  S  S  P  F  Y  C  Q  P  C  L  D  C
```

FIG.1A

```
         670                  690                   710
GCGGGGCCCTGCACCGCCACACACGGCTACTCTGTTCCCGCAGAGATACTGACTGTGGGA
  G  A  L  H  R  H  T  R  L  L  C  S  R  R  D  T  D  C  G  T 730                  750                   770
CCTGCCTGCCTGGCTTCTATGAACATGGCGATGGCTGCGTGTCCTGCCCCACGAGCACCC
  C  L  P  G  F  Y  E  H  G  D  G  C  V  S  C  P  T  S  T  L 790                  810                   830
TGGGGAGCTGTCCAGAGCGCTGTGCCGCTGTCTGTGGCTGGAGGCAGATGTTCTGGGTCC
  G  S  C  P  E  R  C  A  A  V  C  G  W  R  Q  M  F  W  V  Q 850                  870                   890
AGGTGCTCCTGGCTGGCCTTGTGGTCCCCCTCCTGCTTGGGGCCACCCTGACCTACACAT
  V  L  L  A  G  L  V  V  P  L  L  L  G  A  T  L  T  Y  T  Y 910                  930                   950
ACCGCCACTGCTGGCCTCACAAGCCCCTGGTTACTGCAGATGAAGCTGGGATGGAGGCTC
  R  H  C  W  P  H  K  P  L  V  T  A  D  E  A  G  M  E  A  L 970                  990                  1010
TGACCCCACCACCGGCCACCCATCTGTCACCCTTGGACAGCGCCCACACCCTTCTAGCAC
  T  P  P  P  A  T  H  L  S  P  L  D  S  A  H  T  L  L  A  P 1030                 1050                  1070
CTCCTGACAGCAGTGAGAAGATCTGCACCGTCCAGTTGGTGGGTAACAGCTGGACCCCTG
  P  D  S  S  E  K  I  C  T  V  Q  L  V  G  N  S  W  T  P  G 1090                 1110                  1130
GCTACCCCGAGACCCAGGAGGCGCTCTGCCCGCAGGTGACATGGTCCTGGGACCAGTTGC
  Y  P  E  T  Q  E  A  L  C  P  Q  V  T  W  S  W  D  Q  L  P 1150                 1170                  1190
CCAGCAGAGCTCTTGGCCCCGCTGCTGCGCCCCACACTCTCGCCAGAGTCCCCAGCCGGCT
  S  R  A  L  G  P  A  A  A  P  T  L  S  P  E  S  P  A  G  S 1210                 1230                  1250
CGCCAGCCATGATGCTGCAGCCGGGCCCGCAGCTCTACGACGTGATGGACGCGGTCCCAG
  P  A  M  M  L  Q  P  G  P  Q  L  Y  D  V  M  D  A  V  P  A 1270                 1290                  1310
CGCGGCGCTGGAAGGAGTTCGTGCGCACGCTGGGGCTGCGCGAGGCAGAGATCGAAGCCG
  R  R  W  K  E  F  V  R  T  L  G  L  R  E  A  E  I  E  A  V
```

FIG. 1B

```
              1330              1350              1370
TGGAGGTGGAGATCGGCCGCTTCCGAGACCAGCAGTACGAGATGCTCAAGCGCTGGCGCC
 E  V  E  I  G  R  F  R  D  Q  Q  Y  E  M  L  K  R  W  R  Q 1390              1410              1430
AGCAGCAGCCCGCGGGCCTCGGAGCCGTTTACGCGGCCCTGGAGCGCATGGGGCTGGACG
 Q  Q  P  A  G  L  G  A  V  Y  A  A  L  E  R  M  G  L  D  G 1450              1470              1490
GCTGCGTGGAAGACTTGCGCAGCCGCCTGCAGCGCGGCCCGTGACACGGCGCCCACTTGC
 C  V  E  D  L  R  S  R  L  Q  R  G  P  *

1510              1530              1550
CACCTAGGCGCTCTGGTGGCCCTTGCAGAAGCCCTAAGTACGGTTACTTATGCGTGTAGA 1570              1590              1610
CATTTTATGTCACTTATTAAGCCGCTGGCACGGCCCTGCGTAGCAGCACCAGCCGGCCCC 1630              1650              1670
ACCCCTGCTCGCCCCTATCGCTCCAGCCAAGGCGAAGAAGCACGAACGAATGTCGAGAGG 1690              1710              1730
GGGTGAAGACATTTCTCAACTTCTCGGCCGGAGTTTGGCTGAGATCGCGGTATTAAATCT 1750              1770
GTGAAAGAAAACAAAACAAAACAAAAAAAAAAAAAAAAAAAAA
```

FIG. 1C

```
  1  ATGGAGCAGC GGCCGCGGGG CTCCGCGGCG GTGGCGGCGG CGCTCCTCCT GGTGCTGCTG
     M  E  Q  R   P  R  G   C  A  A    V  A  A  A   L  L  L    V  L  L

61  GGGGCCCGGG CCCAGGGCGG CACTCGTAGC CCCAGGTGTG ACTGTGCCGG TGACTTCCAC
     G  A  R  A   Q  G  G   T  R  S    P  R  C  D   C  A  G    D  F  H

121  AAGAAGATTG GTCTGTTTTG TTGCAGAGGC TGCCCAGCGG GGCACTACCT GAAGGCCCCT
     K  K  I  G   L  F  C    C  R  G    C  P  A  G    H  Y  L    K  A  P

181  TGCACGGAGC CCTGCGGCAA CTCCACCTGC CTTGTGTGTC CCCAAGACAC CTTCTTGGCC
     C  T  E  P   C  G  N    S  T  C    L  V  C    P  Q  D  T   F  L  A

241  TGGGAGAACC ACCATAATTC TGAATGTGCC CGCTGCCAGG CCTGTGATGA GCAGGCCTCC
     W  E  N  H   H  N  S    E  C  A    R  C  Q  A   C  D  E    Q  A  S

301  CAGGTGGCGC TGGAGAACTG TTCAGCAGTG GCCGACACCC GCTGTGGCTG TAAGCCAGGC
     Q  V  A  L   E  N  C    S  A  V    A  D  T  R    C  G  C    K  P  G

361  TGGTTTGTGG AGTGCCAGGT CAGCCAATGT GTCAGCAGTT CACCCTTCTA CTGCCAACCA
     W  F  V  E   C  Q  V    S  Q  C    V  S  S    P  F  Y    C  Q  P

421  TGCCTAGACT GCGGGGCCCT GCACCGCCAC ACACGGCTAC TCTGTTCCCG CAGAGATACT
     C  L  D  C   G  A  L    H  R  H    T  R  L  L    C  S  R    R  D  T

481  GACTGTGGGA CCTGCCTGCC TGGCTTCTAT GAACATGGCG ATGGCTGCGT GTCCTGCCCC
     D  C  G  T    C  L  P    G  F  Y    E  H  G  D   G  C  V    S  C  P

541  ACGAGCACCC TGGGGAGCTG TCCAGAGCGC TGTGCCGCTG TCTGTGGCTG GAGGCAGATG
     T  S  T  L   G  S  C    P  E  R    C  A  A  V   C  G  W    R  Q  M

601  TTCTGGGTCC AGGTGCTCCT GGCTGGCCTT GTGGTCCCCC TCCTGCTTGG GGCCACCCTG
     F  W  V  Q   V  L  L    A  G  L    V  V  P    L  L  L  G    A  T  L

661  ACCTACACAT ACCGCCACTG CTGGCCTCAC AAGCCCCTGG TTACTGCAGA TGAAGCTGGG
     T  Y  T  Y   R  H  C    W  P  H    K  P  L  V   T  A  D    E  A  G

721  ATGGAGGCTC TGACCCCACC ACCGGCCACC CATCTGTCAC CCTTGGACAG CGCCCACACC
     M  E  A  L   T  P  P    P  A  T    H  L  S  P   L  D  S    A  H  T

781  CTTCTAGCAC CTCCTGACAG CAGTGAGAAG ATCTGCACCG TCCAGTTGGT GGGTAACAGC
     L  L  A  P    P  D  S    S  E  K    I  C  T  V   Q  L  V    G  N  S
```

FIG.2A

```
841  TGGACCCCTG GCTACCCCGA GACCCAGGAG GCGCTCTGCC CGCAGGTGAC ATGGTCCTGG
      W  T  P  G   Y  P  E    T  Q  E    A  L  C  P    Q  V  T    W  S  W

901  GACCAGTTGC CCAGCAGAGC TCTTGGCCCC GCTGCTGCGC CCACACTCTC GCCAGAGTCC
      D  Q  L  P   S  R  A    L  G  P    A  A  A  P    T  L  S    P  E  S

961  CCAGCCGGCT CGCCAGCCAT GATGCTGCAG CCGGGCCCGC AGCTCTACGA CGTGATGGAC
      P  A  G  S   P  A  M    M  L  Q    P  G  P    Q  L  Y  D    V  M  D

1021 GCGGTCCCAG CGCGGCGCTG GAAGGAGTTC GTGCGCACGC TGGGGCTGCG CGAGGCAGAG
      A  V  P  A   R  R  W    K  E  F    V  R  T  L    G  L  R    E  A  E

1081 ATCGAAGCCG TGGAGGTGGA GATCGGCCGC TTCCGAGACC AGCAGTACGA GATGCTCAAG
      I  E  A  V   E  V  E    I  G  R    F  R  D  Q    Q  Y  E    M  L  K

1141 CGCTGGCGCC AGCAGCAGCC CGCGGGCCTC GGAGCCGTTT ACGCGGCCCT GGAGCGCATG
      R  W  R  Q   Q  Q  P    A  G  L    G  A  V  Y    A  A  L    E  R  M

1201 GGGCTGGACG GCTGCGTGGA AGACTTGCGC AGCCGCCTGC AGCGCGGCCC GTGA
      G  L  D  G   C  V  E    D  L  R    S  R  L  Q    R  G  P
```

FIG.2B

```
Consensus #1    M . . . . . . . . . . . . . . . . . . . . . . . . . . . L .
DDCR            M E E T Q Q G E A P R G Q L R G E S A A P V P Q A L L V L   30
TNFR1           M G L S T V P D L L L P L V L L E L L V G I Y P S G V I G L 30
FAS             M - L G I W T L L P L V L T S V A R L S S K S V N A Q V T D 29

Consensus #1    . . . . . . . . . . . . . . . . . . . . . . . . . . . C . .
DDCR            L G A R A Q G G T R S P R C D C A G D F H - - K K I G L F C 58
TNFR1           V P H L G D R E K R D S V C P Q G K Y I H - - P Q N N S I C 58
FAS             I N S K G L E L R K T V T T V E T Q N L E G L H H D G Q F C 59

Consensus #1    . . . C . . G . . . . . . . . . . . H . . . . . C . . C . .
DDCR            C R G C P A G H Y L K A P C T E P C G N S T C L V C P Q D T 88
TNFR1           C T K C H K G T Y L Y N D C P G P G Q D T D C R E C E S G S 88
FAS             H K P C P P G E R K A R D C T V N G D E P D C V P C Q E G K 89

Consensus #1    . . . . . . . . . . . . . . . . . . . . . . . . . C . . C .
DDCR            F L A W E N H H N S E C A R C Q A C D E Q A S Q V A L E N C 118
TNFR1           F T A S E N H L R - H C L S C S K C R K E M G Q V E I S S C 117
FAS             E Y T D K A H F S S K C R R C R L C D E G H G L E V E I N C 119
```

FIG.3A

```
Consensus #1   .  .  .  .  .  .  .  .  .  .  .  .  .  .  .  .  .  .  . T . C . C .  .  .  .  .  .  .  .  .  .  .  .  .  .

DDCR           S A V A D T R C G C K P G W E V E C - - - Q V S Q C V S S S  145
TNFR1          T V D R D T V C G C R K N Q Y R H Y W S E N L F Q C - - - -  144
FAS            R T Q N T K C R C K P N F F Q N - - - - - - - - - - - - - -  137

Consensus #1   .  .  .  .  .  .  .  .  .  .  .  .  C  .  .  .  .  .  .  .  .  .  .  .  .  .  .  .  .  .  .  .  .

DDCR           P F Y C Q P C L D C G A L H R H T R L L C S R R D T D C G T  175
TNFR1          - F N C S L C L N - G T V H - - - L S C Q E K Q N T V C I -  167
FAS            - - - S T V C E H C D P - - - - - - - - - - - - C T K - - -  148

Consensus #1   .  .  .  .  .  .  .  .  .  C  .  .  G  .  .  .  .  .  .  .  .  C  .  .  .  .  .  .  .  .  .  .  .

DDCR           C L P G F Y E H G D G C V S C P T S T L G - S C P E R C - -  203
TNFR1          C H A G F F L R E N E C V S C S N C K K S L E C T K L C L P  197
FAS            C E H G T I - - - K E C - - - - - - - T L T S N T K C - - -  166

Consensus #1   .  .  .  .  .  .  .  .  .  .  .  .  .  .  .  .  .  .  .  .  .  .  .  .  .  .  .  .  .  L  .

DDCR           - - - - - A A V C G W R Q M F W V Q V L L A G L V V P L       225
TNFR1          Q I E N V K G T E D S G T T V L L P L V I F F G L C L L S L   227
FAS            - - - K E E G S R S N L G W L C L L - - L P I P L             186
```

FIG.3B

```
Consensus #1         .    .    .    .    .    .    .
DDCR         L L G T L D L H I P P L L A H K P L V T A D E A G M E A L   255
TNFR1        L F I G - L M R Y Q R W K S K L Y S I V C G S T P E K E     256
FAS          I V - - - - - - - - - - W V K R K E V - - Q K T C R K H R   203

Consensus #1         .    .    G    .    .    P    .    .    .
DDCR         N P P P G T H L S P L D S A H T L L A P P D S S E K I C T V   285
TNFR1        G E L E G T T T K P L A P N P S F S P T P G F T P T L G F S   286
FAS          K E N Q G S H E S P - - - - - - - - - - - - - - - - - - -   214

Consensus #1         .    .    .    .    .    .    .
DDCR         Q L V G N S W T P G Y P E T Q E A L C P Q V T W S W D Q L -   315
TNFR1        P V P S S T F I S S S T Y T I P G D - C P N F A A P R R E V A   315
FAS          - - - - - - - - - - - - - - - - - - - - - - - - - - - - -   214

Consensus #1         .    .    .    L    .    .    .    .    .
DDCR         - P S R A L G P A A A P T L S P E S P A G S - - - - - - - -   336
TNFR1        P P Y Q G A D P I L A T A L A S D P I P N P L Q K W E D S A   345
FAS          - - - - - - - - - - - T L N P E T V A I N L S - - - - - - -   226
```

FIG. 3C

```
Consensus #1                                                              K . F V
DDCR        - - - P A M M L Q P G P Q L Y D V M D A V P A R R W K E F V   362
TNFR1       H K P Q S L D T D D P A T L Y A V E N V P P L R W K E F V     375
FAS         - - - - D V D L S K Y I T T I A G V M T L S Q V K G F V       249

Consensus #1              R . . G . . . . . I . . . . . . . . . . . L .

DDCR        R T L G L R E A E I E A V E V E I G R - F R D Q Q Y E M L K   391
TNFR1       R R L G L S D H E I D R L E L Q N G R C L R E A Q Y S M L A   405
FAS         R K N G V N E A K I D E I K N D N V Q D T A E Q K V Q L L R   279

Consensus #1        . W . . . . . A . . . . . . . . . . . . . . L . . E

DDCR        R W R Q Q Q P - - A G L G A V Y A A L E R M G L D G C V E     418
TNFR1       T W R R R T P R R E A T L E L L G R V L R D M D L L G C L E   435
FAS         N W H Q L H G K K E A - Y D T L I K D L K K A N L C T L A E   308

Consensus #1

DDCR        D L - - - - - - - - - - - R S R L Q R G P                     428
TNFR1       D I E E A L - - - - - - - C G P A A L P P A P S L L R         455
FAS         K I Q T I I L K D I T S D S E N S N F R N E I Q S L V         335
```

FIG.3D

DEATH DOMAIN CONTAINING RECEPTORS

CROSS-REFERENCE TO RELATED APPLICATIONS

The present application is a divisional of U.S. application Ser. No. 08/815,469, filed Mar. 11, 1997, now U.S. Pat. No. 6,153,402 which is herein incorporated by reference: said Ser. No. 08/815,469 claims priority to U.S. Provisional Application No. 60/013,285, filed Mar. 12, 1996, U.S. Provisional Application No. 60/028,711, filed Oct. 17, 1996, and U.S. Provisional Application No. 60/037,341, filed Feb. 6, 1997, each of which is herein incorporated by reference.

BACKGROUND OF THE INVENTION

1. Field of the Invention

The present invention relates to a novel member of the tumor necrosis factor family of receptors. More specifically, isolated nucleic acid molecules are provided encoding human Death Domain Containing Receptors (DR3 and DR3-V1). Death Domain Containing Receptor polypeptides are also provided, as are vectors, host cells and recombinant methods for producing the same. The invention further relates to screening methods for identifying agonists and antagonists of DR3 activity.

2. Related Art

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNFα, lymphotoxin-α (LTα, also known as TNF-β), LT-β (found in complex heterotrimer LT-α2-β), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (A. Meager, *Biologicals*, 22:291–295 (1994)).

Many members of the TNF-ligand superfamily are expressed by activated T-cells, implying that they are necessary for T-cell interactions with other cell types which underlie cell ontogeny and functions. (A. Meager, supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (R Watanabe-Fukunaga et al., *Nature* 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (R. C. Allen et al., *Science* 259:990 (1993)). Targeted mutations of the low affinity nerve growth factor receptor cause a disorder characterized by faulty sensory innovation of peripheral structures (K. F. Lee et al., *Cell* 69:737 (1992)).

TNF and LT-α are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and antiviral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (B. Beutler and C. Von Huffel, *Science* 264:667–668 (1994)). Mutations in the p55 receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., *Cell* 74:845 (1993)).

Apoptosis, or programmed cell death, is a physiologic process essential to the normal development and homeostasis of multicellular organisms (H. Steller, *Science* 267, 1445–1449 (1995)). Derangements of apoptosis contribute to the pathogenesis of several human diseases including cancer, neurodegenerative disorders, and acquired immune deficiency syndrome (C. B. Thompson, *Science* 267, 1456–1462 (1995)). Recently, much attention has focused on the signal transduction and biological function of two cell surface death receptors, Fas/APO-1 and TNFR-1 (J. L. Cleveland et al., *Cell* 81, 479482 (1995); A. Fraser et al., *Cell* 85, 781–784 (1996); S. Nagata et al., *Science* 267, 1449–56 (1995)). Both are members of the TNF receptor family which also include TNFR-2, low affinity NGFR, CD40, and CD30, among others (C. A. Smith et al., *Science* 248, 1019–23 (1990); M. Tewari et al., in *Modular Texts in Molecular and Cell Biology* M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain," which is distantly related to the Drosophila suicide gene, reaper (P. Golstein et al., *Cell* 81, 185–6 (1995); K. White et al., *Science* 264, 677–83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan et al., *Cell* 81, 505–12 (1995); M. P. Boldin et al., *J. Biol Chem* 270, 7795–8 (1995); F. C. Kischkel et al., *EMBO* 14, 5579–5588 (1995)), which in turn binds and presumably activates FLICE/MACH1, a member of the ICE/CED-3 family of pro-apoptotic proteases (M. Muzio et al., *Cell* 85, 817–827 (1996); M. P. Boldin et al., *Cell* 85, 803–815 (1996)). While the central role of Fas/APO-1 is to trigger cell death, TNFR-1 can signal an array of diverse biological activities-many of which stem from its ability to activate NF-kB (L. A. Tartaglia et al., *Immunol Today* 13, 151–3 (1992)). Accordingly, TNFR-1 recruits the multivalent adapter molecule TRADD, which like FADD, also contains a death domain (H. Hsu et al., *Cell* 81, 495–504 (1995); H. Hsu et al., *Cell* 84, 299–308 (1996)). Through its associations with a number of signaling molecules including FADD, TRAF2, and RIP, TRADD can signal both apoptosis and NF-kB activation, Id; H. Hsu et al., *Immunity* 4, 387–396 (1996)).

The effects of family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize novel members of the TNF receptor family.

SUMMARY OF THE INVENTION

The present invention provides for isolated nucleic acid molecules comprising nucleic acid sequences encoding the amino acid sequences shown in FIGS. 1A–1C (SEQ ID NO:2) and FIGS. 2A–2B (SEQ ID NO:4) or the amino acid sequence encoding the cDNA clones deposited as ATCC Deposit No. 97456 on Mar. 1, 1996 and ATCC Deposit No. 97757 on Oct. 10, 1996.

The present invention also provides vectors and host cells for recombinant expression of the nucleic acid molecules described herein, as well as to methods of making such vectors and host cells and for using them for production of DR3 or DR3 Variant 1 (DR3-V1) (formerly named DDCR) polypeptides or peptides by recombinant techniques.

The invention further provides an isolated DR3 or DR3-V1 polypeptide having an amino acid sequence encoded by a polynucleotide described herein.

The present invention also provides diagnostic assays such as quantitative and diagnostic assays for detecting levels of DR3 or DR3-V1 protein. Thus, for instance, a diagnostic assay in accordance with the invention for detecting over-expression of DR3 or DR3-V1, or soluble form thereof, compared to normal control tissue samples may be used to detect the presence of tumors.

Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes. Cellular response to TNF-family ligands include not only normal physiological responses, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft v. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia and anorexia.

Thus, the invention further provides a method for enhancing apoptosis induced by a TNF-family ligand, which involves administering to a cell which expresses the DR3 polypeptide an effective amount of an agonist capable of increasing DR3 mediated signaling. Preferably, DR3 mediated signaling is increased to treat a disease wherein decreased apoptosis is exhibited.

In a further aspect, the present invention is directed to a method for inhibiting apoptosis induced by a TNF-family ligand, which involves administering to a cell which expresses the DR3 polypeptide an effective amount of an antagonist capable of decreasing DR3 mediated signaling. Preferably, DR3 mediated signaling is decreased to treat a disease wherein increased apoptosis is exhibited.

Whether any candidate "agonist" or "antagonist" of the present invention can enhance or inhibit apoptosis can be determined using art-known TNF-family ligand/receptor cellular response assays, including those described in more detail below. Thus, in a further aspect, a screening method is provided for determining whether a candidate agonist or antagonist is capable of enhancing or inhibiting a cellular response to a TNF-family ligand. The method involves contacting cells which express the DR3 or DR3-V1 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing the DR3 or DR3-V1 polypeptide can be contacted with either an endogenous or exogenously administered TNF-family ligand.

BRIEF DESCRIPTION OF THE FIGURES

FIGS. 1A–1C shows the nucleotide and deduced amino acid sequence of DR3-V1. It is predicted that amino acids 1–35 constitute the signal peptide, amino acids 36–212 constitute the extracellular domain, amino acids 213–235 constitute the transmembrane domain, amino acids 236428 constitute the intracellular domain, and amino acids 353419 the death domain.

FIGS. 2A–2B shows the nucleotide and deduced amino acid sequence of DR3. It is predicted that amino acids 1–24 constitute the signal peptide, amino acids 25–201 constitute the extracellular domain, amino acids 202–224 constitute the transmembrane domain, amino acids 225–417 constitute the intracellular domain, and amino acids 342–408 constitute the death domain.

FIGS. 3A–3D shows the regions of similarity between the amino acid sequences of the DR3-V1, human tumor necrosis factor receptor 1, and Fas receptor [SEQ ID NOS:5 and 6] Consensus #1: When all match the residue of the Consensus, the residue of the Consensus is shown, other a "." is shown. Residues that match the Consensus exactly are boxed.

DETAILED DESCRIPTION OF THE PREFERRED EMBODIMENTS

Figure 4:
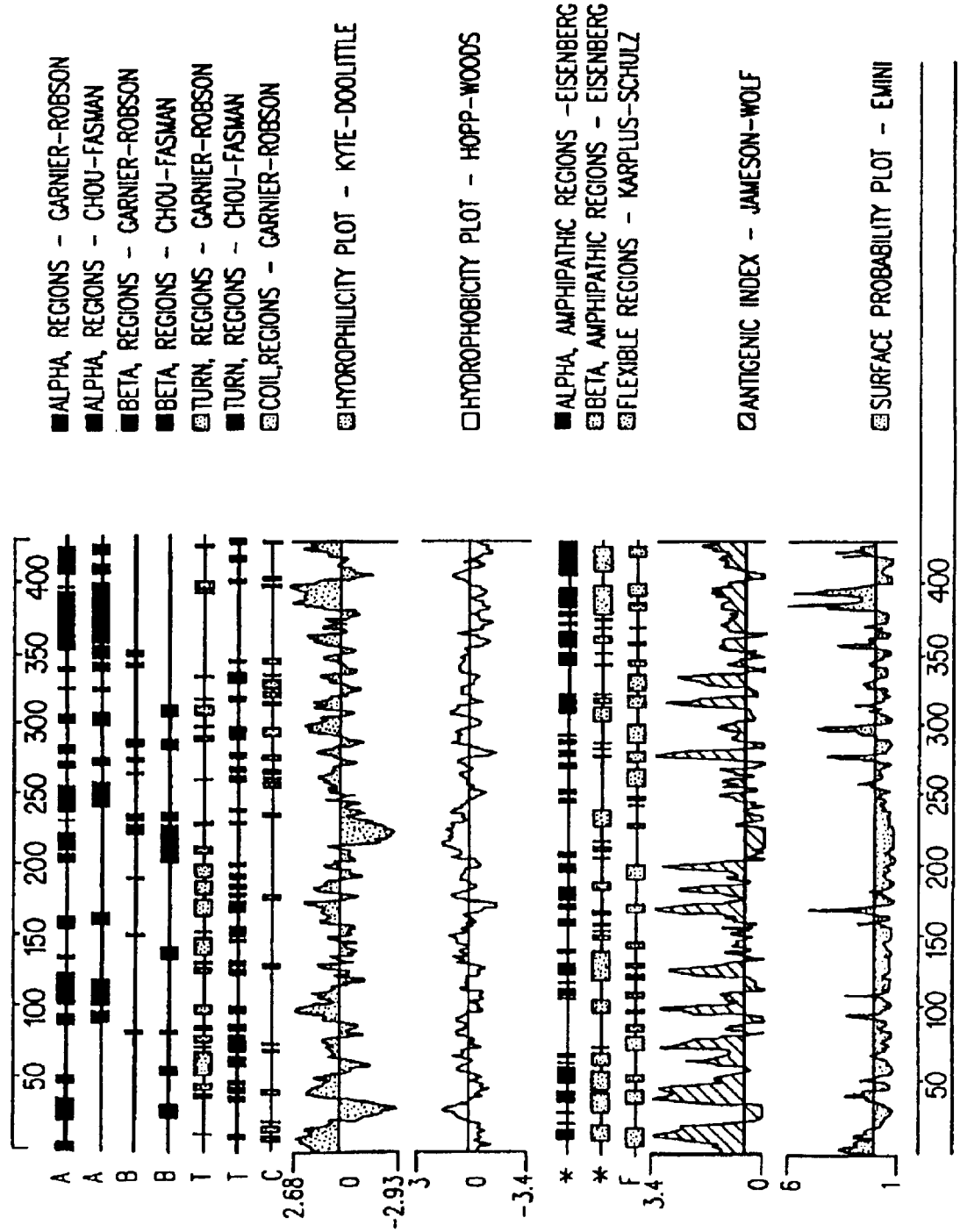
FIG. 4 shows an analysis of the DR3-V1 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues1-22, 33–56, 59–82, 95–112, 122–133, 161–177, 179–190, 196–205 in FIGS. 1A–1C correspond to the shown highly antigenic regions of the DR3-V1 protein.

The present invention provides isolated nucleic acid molecules comprising a nucleic acid sequence encoding the DR3-V1 or DR3 polypeptide whose amino acid sequence is shown in FIGS. 1A–1C [SEQ ID NO:2] and FIGS. 2A–2B [SEQ ID NO:4], respectively, or a fragment of the polypeptide. The DR3-V1 and DR3 polypeptides of the present invention share sequence homology with human TNF RI and Fas (FIG. 4). The nucleotide sequence shown in FIGS.

1A–1C [SEQ ID NO:1] was obtained by sequencing the HTTNB61 clone, which was deposited on Mar. 1, 1996 at the American Type Culture Collection, 10801 University Blvd., Manassas, Va. 20110-2209, USA and given Accession Number 97456. The deposited clone is contained in the pBluescript SK(−) plasmid (Stratagene, LaJolla, Calif.). The nucleotide sequence shown in FIGS. 2A–2B [SEQ ID NO:3] was obtained by sequencing a clone obtained from a HUVEC library, which was deposited on Oct. 10, 1996 at the American Type Culture Collection,10801 University Blvd., Manassas, Va. 20110/2209, USA and given Accession Number 97757. The deposited clone is contained in the pBluescript SK(−) plasmid (Stratagene, LaJolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "isolated" polypeptide or protein is intended a polypeptide or protein removed from its native environment. For example, recombinantly produced polypeptides and proteins expressed in host cells are considered isolated for purposes of the invention, as are native or recombinant polypeptides which have been substantially purified by any suitable technique such as, for example, the single-step purification method disclosed in Smith and Johnson, *Gene* 67:31–40 (1988).

Using the information provided herein, such as the nucleic acid sequence set out in FIGS. 1A–1C or FIGS. 2A–2B, a nucleic acid molecule of the present invention encoding a DR3-V1 or DR3 polypeptide may be obtained using standard cloning and screening procedures, such as those for cloning cDNAs using mRNA as starting material. Illustrative of the invention, the nucleic acid molecule described in FIGS. 1A–1C was discovered in a cDNA library derived from cells of a human testis tumor. Also illustrative of the invention, the nucleic acid molecule described in FIGS. 2A–2B was discovered in a human HUVEC cDNA library. In addition, the genes of the present invention have also been identified in cDNA libraries of the following tissues: fetal liver, fetal brain, tonsil and leukocyte. Furthermore, multiple forms of DR3 transcript are seen in Northern Blots and PCR reactions indicating that multiple variants of the transcript exists, possibly due to alternate splicing of the message.

The DR3-V1 (formerly called DDCR) gene contains an open reading frame encoding a protein of about 428 amino acid residues whose initiation codon is at position 198–200 of the nucleotide sequence shown in FIGS. 1A–1C [SEQ ID NO.1], with a leader sequence of about 35 amino acid residues, and a deduced molecular weight of about 47 kDa. Of known members of the TNF receptor family, the DR3-V1 polypeptide of the invention shares the greatest degree of homology with human TNF R1 . The DR3-V1 polypeptide shown in FIGS. 1A–1C [SEQ ID NO:2] is about 20% identical and about 50% similar to human TNF R1 .

The DR3 gene contains an open reading frame encoding a protein of about 417 amino acid residues whose initiation codon is at position 1–3 of the nucleotide sequence shown in FIGS. 2A–2B [SEQ ID NO:3], with a leader sequence of about 24 amino acid residues, and a deduced molecular weight of about 43 kDa. Of known members of the TNF receptor family, the DR3 polypeptide of the invention shares the greatest degree of homology with human TNF R1 . The DR3 polypeptide shown in FIGS. 2A–2B [SEQ ID NO:3] is about 20% identical and about 50% similar to human TNF R1 .

As indicated, the present invention also provides the mature form(s) of the DR3-V1 and DR3 protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature DR3-V1 or DR3 polypeptides having the amino acid sequence encoded by the cDNA clones contained in the host identified as ATCC Deposit No. 97456 and 97757, respectively, and as shown in FIGS. 1A–1C (SEQ ID NO:2) and FIGS. 2A–2B (SEQ ID NO:4). By the mature DR3-V1 or DR3 protein having the amino acid sequence encoded by the cDNA clones contained in the host identified as ATCC Deposit No. 97456 and 97757, respectively, is meant the mature form(s) of the DR3-V1 or DR3 protein produced by expression in a mammalian cell (e.g., COS cells, as described below) of the complete open reading frame encoded by the human DNA sequence of the clone contained in the vector in the deposited host. As indicated below, the mature DR3-V1 or DR3 having the amino acid sequence encoded by the cDNA clones contained in ATCC Deposit No. 97456 and 97757, respectively, may or may not differ from the predicted "mature" DR3-V1 protein shown in FIGS. 1A–1C (amino acids from about 36 to about 428) or DR3 protein shown in FIGS. 2A–2B (amino acids from about 24 to about 417) depending on the accuracy of the predicted cleavage site based on computer analysis.

Methods for predicting whether a protein has a secretory leader as well as the cleavage point for that leader sequence are available. For instance, the method of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequences of the complete DR3-V1 and DR3 polypeptides of the present invention were analyzed by a computer program ("PSORT"), see, K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids 35 and 36 in FIGS. 1A–1C (SEQ ID NO:2) and between amino acids 24 and 25 in FIGS. 2A–2B (SEQ ID NO:4). Thereafter, the complete amino acid sequences were further analyzed by visual inspection, applying a simple form of the (−1,−3) rule of von Heine. von Heinje, supra. Thus, the leader sequence for the DR3-V1 protein is predicted to consist of amino acid residues 1–35 in FIGS. 1A–1C (SEQ ID NO:2), while the predicted mature DR3-V1 protein consists of residues 36428. The leader sequence for the DR3 protein is predicted to consist of amino acid residues 1–24 in FIGS. 2A–2B (SEQ ID NO:4), while the predicted mature DR3 protein consists of residues 25–417.

As one of ordinary skill would appreciate, due to the possibilities of sequencing errors discussed above, as well as the variability of cleavage sites for leaders in different known proteins, the actual DR3-V1 polypeptide encoded by the deposited cDNA comprises about 428 amino acids, but may be anywhere in the range of 410–440 amino acids; and the actual leader sequence of this protein is about 35 amino acids, but may be anywhere in the range of about 25 to about 45 amino acids. The actual DR3 polypeptide encoded by the deposited cDNA comprises about 417 amino acids, but may be anywhere in the range of 400–430 amino acids; and the actual leader sequence of this protein is about 24 amino acids, but may be anywhere in the range of about 14 to about 34 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DR3-V1 DNA molecules comprising an open reading frame (ORF) shown in FIGS. 1A–1C [SEQ ID NO:1] and further include DNA molecules which comprise a sequence substantially different than all or part of the ORF whose initiation codon is at position 198–200 of the nucleotide sequence shown in FIGS. 1A–1C [SEQ ID NO:1] but which, due to the degeneracy of the genetic code, still encode the DR3-V1 polypeptide or a fragment thereof. Isolated nucleic acid molecules of the present invention also include DR3 DNA molecules comprising an open reading frame (ORF) shown in FIGS. 2A–2B [SEQ ID NO:3] and further include DNA molecules which comprise a sequence substantially different than all or part of the ORF whose initiation codon is at position 1–3 of the nucleotide sequence shown in FIGS. 2A–2B [SEQ ID NO:3] but which, due to the degeneracy of the genetic code, still encode the DR3 polypeptide or a fragment thereof Of course, the genetic code is well known in the art. Thus, it would be routine for one skilled in the art to generate such degenerate variants.

In another aspect, the invention provides isolated nucleic acid molecules encoding the DR3-V1 polypeptide having an amino acid sequence encoded by the cDNA clone contained in the plasmid deposited as ATCC Deposit No. 97456 on Mar. 1, 1996. The invention provides isolated nucleic acid molecules encoding the DR3 polypeptide having an amino acid sequence encoded by the cDNA clone contained in the plasmid deposited as ATCC Deposit No. 97757 on Oct. 10, 1996. Preferably, these nucleic acid molecules will encode the mature polypeptide encoded by the above-described deposited cDNA clone. The invention further provides an isolated nucleic acid molecule having the nucleotide sequence shown in FIGS. 1A–1C (SEQ ID NO:1) or FIGS. 2A–2B (SEQ ID NO:3) or the nucleotide sequence of the DR3-V1 or DR3 cDNA contained in the above-described deposited clone, or a nucleic acid molecule having a sequence complementary to one of the above sequences. Such isolated DNA molecules and fragments thereof are useful as DNA probes for gene mapping by in situ hybridization with chromosomes, and for detecting expression of the DR3-V1 or DR3 gene in human tissue (including testis tumor tissue) by Northern blot analysis.

The present invention is further directed to fragments of the isolated nucleic acid molecules described herein. By fragments of an isolated DNA molecule having the nucleotide sequence shown in FIGS. 1A–1C [SEQ ID NO:1] or FIGS. 2A–2B [SEQ ID NO:3] are intended DNA fragments at least 20 bp, and more preferably at least 30 bp in length, which are useful as DNA probes as discussed above. Of course larger DNA fragments 50–1500 bp in length are also useful as DNA probes according to the present invention, as are DNA fragments corresponding to most, if not all, of the nucleotide sequence shown in FIGS. 1A–1C [SEQ ID NO:1] or FIGS. 2A–2B [SEQ ID NO:3]. By a fragment at least 20 bp in length, for example, is intended fragments which include 20 or more bases from the nucleotide sequence in FIGS. 1A–1C [SEQ ID NO:1] or FIGS. 2A–2B [SEQ ID NO:3].

Preferred nucleic acid fragments of the present invention include nucleic acid molecules encoding: a polypeptide comprising the DR3-V1 extracellular domain (amino acid residues from about 36 to about 212 in FIGS. 1A–1C [SEQ ID NO:2]); a polypeptide comprising the DR3-V1 transmembrane domain (amino acid residues from about 213 to about 235 in FIGS. 1A–1C [SEQ ID NO:2]; a polypeptide comprising the DR3-V1 intracellular domain (amino acid residues from about 236 to about 428 in FIGS. 1A–1C [SEQ ID NO:2]; and a polypeptide comprising the DR3-V1 death domain (amino acid residues from about 353 to about 419 in FIGS. 1A–1C [SEQ ID NO:2]). Since the location of these domains have been predicted by computer graphics, one of ordinary skill would appreciate that the amino acid residues constituting these domains may vary slightly (e.g., by about 1 to 15 residues) depending on the criteria used to define the domain.

Preferred nucleic acid fragments of the present invention also include nucleic acid molecules encoding: amino acid residues from about 1 to about 215 of SEQ ID NO:2; amino acid residues from about 30 to about 215 of SEQ ID NO:2; amino acid residues from about 215 to about 240 of SEQ ID NO:2; amino acid residues from about 240 to about 428 of SEQ ID NO:2; and amino acid residues from about 350 to about 420 of SEQ ID NO:2.

Preferred nucleic acid fragments of the present invention further include nucleic acid molecules encoding epitope-bearing portions of the DR3-V1 protein. In particular, such nucleic acid fragments of the present invention include nucleic acid molecules encoding: a polypeptide comprising amino acid residues from about 1 to about 22 in FIGS. 1A–1C (SEQ ID NO:2); a polypeptide comprising amino acid residues from about 33 to about 56 in FIGS. 1A–1C (SEQ ID NO:2); a polypeptide comprising amino acid residues from about 59 to about 82 in FIGS. 1A–1C (SEQ ID NO:2); a polypeptide comprising amino acid residues from about 95 to about 112 in FIGS. 1A–1C (SEQ ID NO:2); a polypeptide comprising amino acid residues from about 122 to about 133 in FIGS. 1A–1C (SEQ ID NO:2); a polypeptide comprising amino acid residues from about 161 to about 177 in FIGS. 1A–1C (SEQ ID NO:2); a polypeptide comprising amino acid residues from about 179 to about 190 in FIGS. 1A–1C (SEQ ID NO:2); and a polypeptide comprising amino acid residues from about 196 to about 205 in FIGS. 1A–1C (SEQ ID NO:2). The inventors have determined that the above polypeptide fragments are antigenic regions of the DR3-V1 protein. Methods for determining other such epitope-bearing portions of the DR3-V1 protein are described in detail below.

Preferred nucleic acid fragments of the present invention also include nucleic acid molecules encoding epitope-bearing portions of the DR3 protein. In particular, such nucleic acid fragments of the present invention include nucleic acid molecules encoding the corresponding regions to those epitope-bearing regions of the DR3-V1 protein disclosed above. Methods for determining other such epitope-bearing portions of the DR3 protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clones contained in ATCC Deposit 97456 or ATCC Deposit 97757. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 mg/ml denatured, sheared salmon sperm DNA, followed by washing the filters in 0.×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A–1C (SEQ ID NO:1) or FIGS. 2A–2B (SEQ ID NO:3)).

Of course, a polynucleotide which hybridizes only to a poly A sequence (such as the 3' terminal poly(A) tract of the DR3-V1 cDNA shown in FIGS. 1A–1C (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode the DR3-V1 or DR3 polypeptide may include, but are not limited to the coding sequence for the mature polypeptide, by itself; the coding sequence for the mature polypeptide and additional sequences, such as those encoding a leader or secretary sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad Sci. USA* 86: 821–824 (1989), for instance, hexa-histidine provides for convenient purification of the fusion protein. The HA tag corresponds to an epitope derived of influenza hemagglutinin protein, which has been described by Wilson et al., *Cell* 37:767 (1984), for instance.

The present invention further relates to variants of the nucleic acid molecules of the present invention, which encode for fragments, analogs or derivatives of the DR3-V1 or DR3 polypeptide. Variants may occur naturally, such as an allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions, or additions which may involve one or more nucleotides. The variants may be altered in coding or non-coding regions or both. Alterations in the coding regions may produce conservative or non-conservative amino acid substitutions, deletions, or additions.

Further embodiments of the invention include isolated nucleic acid molecules that are at least 90% identical, and more preferably at least 95%, 96%, 97%, 98% or 99% identical, to (a) a nucleotide sequence encoding the full-length DR3-V1 polypeptide having the complete amino acid sequence in FIGS. 1A–1C (SEQ ID NO:2), including the predicted leader sequence; (b) nucleotide sequence encoding the full-length DR3 polypeptide having the complete amino acid sequence in FIGS. 2A–2B (SEQ ID NO:4), including the predicted leader sequence; (c) a nucleotide sequence encoding the mature DR3-V1 polypeptide (full-length polypeptide with the leader removed) having the amino acid sequence at positions about 36 to about 428 in FIGS. 1A–1C (SEQ ID NO:2); (d) a nucleotide sequence encoding the full-length DR3-V1 polypeptide having the complete amino acid sequence including the leader encoded by the cDNA clone contained in ATCC Deposit No. 97456; (e) a nucleotide sequence encoding the full-length DR3 polypeptide having the complete amino acid sequence including the leader encoded by the cDNA clone contained in ATCC Deposit No. 97757; (f) a nucleotide sequence encoding the mature DR3-V1 polypeptide having the amino acid sequence encoded by the cDNA clone contained in ATCC Deposit No. 97456; (g) a nucleotide sequence encoding the mature DR3-V1 polypeptide having the amino acid sequence encoded by the cDNA clone contained in ATCC Deposit No. 97757; (h) a nucleotide sequence that encodes the DR3 extracellular domain, (i) a nucleotide sequence that encodes the DR3 transmembrane domain, (1) a nucleotide sequence that encodes the DR3 intracellular domain, and (k) a nucleotide sequence that encodes the DR3 death domain; or (1) a nucleotide sequence complementary to any of the nucleotide sequences in (a), (b), (c), (d), (e), (f), (g), (h), (i), 0) or (k) above.

By a polynucleotide having a nucleotide sequence at least, for example, 95% "identical" to a reference nucleotide sequence encoding a DR3-V1 or DR3 polypeptide is intended that the nucleotide sequence of the polynucleotide is identical to the reference sequence except that the polynucleotide sequence may include up to five point mutations per each 100 nucleotides of the reference nucleotide sequence encoding the DR3-V1 or DR3 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A–1C, FIGS. 2A–2B or to the nucleotide sequences of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIGS. 1A–1C (SEQ ID NO:1), FIGS. 2A–2B (SEQ ID NO:3) or to the nucleic acid sequence of the deposited cDNAs, irrespective of whether they encode a polypeptide having DR3 activity. This is because even where a particular nucleic acid molecule does not encode a polypeptide having DR3 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having DDCR activity include, inter alia, (1) isolating the DR3-V1 or DR3 gene or allelic variants thereof in a cDNA library; (2) in situ hybridization (e.g., "FISH") to metaphase chromosomal spreads to provide precise chromosomal location of the DR3-V1 or DR3 gene, as described in Verma et al., *Human Chromosomes: A Manual of Basic Techniques*, Pergamon Press, New York (1988); and (3) Northern Blot analysis for detecting DR3-V1 or DR3 mRNA expression in specific tissues.

Preferred, however, are nucleic acid molecules having sequences at least 90% 95%, 96%, 97%, 98% or 99% identical to the nucleic acid sequence shown in FIGS. 1A–1C (SEQ ID NO:1), FIGS. 2A–2B (SEQ ID NO:3) or to the nucleic acid sequence of the deposited cDNAs which do, in fact, encode a polypeptide having DR3 protein activity. By "a polypeptide having DR3 activity" is intended polypeptides exhibiting activity similar, but not necessarily identical, to an activity of the DR3 protein of the invention (either the full-length protein or, preferably, the mature protein), as measured in a particular biological assay. For example, DR3 protein activity can be measured using the cell death assays performed essentially as previously described (A. M. Chinnaiyan et al., *Cell* 81, 505–12 (1995); M. P. Boldin et al., *J Biol Chem* 270, 7795–8 (1995); F. C. Kischkel et al. *EMBO* 14, 5579–5588 (1995); A. M. Chinnaiyan, et al.,*J Biol Chem* 271, 4961–4965 (1996)), and as set forth in Example 7, below. In MCF7 cells, plasmids encoding full-length DR3 or a candidate death domain containing receptors are co-transfected with the pLantern reporter construct encoding green fluorescent protein. Nuclei of cells transfected with DR3 will exhibit apoptotic morphology as assessed by DAPI staining. Similar to TNFR-1 and Fas/APO-1 (M. Muzio et al., *Cell* 85, 817–827 (1996); M. P. Boldin et al., *Cell* 85, 803–815 (1996); M. Tewari et al., *J Biol Chem* 270, 3255–60 (1995)), DR3-induced apoptosis is blocked by the inhibitors of ICE-like proteases, CrmA and z-VAD-fmk. In addition, apoptosis induced by DR3 is also blocked by dominant negative versions of FADD (FADD-DN) or FLICE (FLICE-DN/MACHa1C360S).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A–1C (SEQ ID NO:1) or FIGS. 2A–2B (SEQ ID NO:3) will encode a polypeptide "having DR3 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having DR3 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science*

247:1306–1310 (1990), wherein the authors indicate that proteins are surprisingly tolerant of amino acid substitutions.

Polynucleotide Assays

This invention is also related to the use of the DR3-V1 or DR3 polynucleotides to detect complementary polynucleotides such as, for example, as a diagnostic reagent. Detection of a mutated form of DR3-V1 or DR3 associated with a dysfunction will provide a diagnostic tool that can add or define a diagnosis of a disease or susceptibility to a disease which results from under-expression over-expression or altered expression of DR3-V1 or DR3 or a soluble form thereof, such as, for example, tumors or autoimmune disease.

Individuals carrying mutations in the DR3-V1 or DR3 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163–166 (1986)). RNA or cDNA may also be used in the same ways. As an example, PCR primers complementary to the nucleic acid encoding DR3-V1 or DR3 can be used to identify and analyze DR3-V1 or DR3 expression and mutations. For example, deletions and insertions can be detected by a change in size of the amplified product in comparison to the normal genotype. Point mutations can be identified by hybridizing amplified DNA to radiolabeled DR3-V1 or DR3 RNA or alternatively, radiolabeled DR3-V1 or DR3 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and S1 protection or the chemical cleavage method (e.g., Cotton et al., *Proc. Natl. Acad Sci. USA* 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Chromosome Assays

The sequences of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a DR3-V1 or a DR3 gene. This can be accomplished using a variety of well known techniques and libraries, which generally are available commercially. The genomic DNA is then used for in situ chromosome mapping using well known techniques for this purpose.

In addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Vectors and Host Cells

The present invention also relates to vectors which include DNA molecules of the present invention, host cells which are genetically engineered with vectors of the invention and the production of polypeptides of the invention by recombinant techniques.

Host cells can be genetically engineered to incorporate nucleic acid molecules and express polypeptides of the present invention. The polynucleotides may be introduced alone or with other polynucleotides. Such other polynucleotides may be introduced independently, co-introduced or introduced joined to the polynucleotides of the invention.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector, or supplied by the vector itself upon introduction into the host.

A great variety of expression vectors can be used to express a polypeptide of the invention. Such vectors include chromosomal, episomal and virus-derived vectors, e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The DNA sequence in the expression vector is operatively linked to appropriate expression control sequence(s), including, for instance, a promoter to direct mRNA transcription. Representatives of such promoters include the phage lambda PL promoter, the *E. Coli* lac, trp and tac promoters, the SV40 early and late promoters and promoters of retroviral LTRs, to name just a few of the well-known promoters. In general, expression constructs will contain sites for transcription, initiation and termination, and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli, Streptomyces* and *Salmonella typhimurium* cells; fungal cells, such as yeast cells; insect cells such as Drosophila S2 and Spodoptera Sf9 cells; animal cells such as CHO, COS, and Bowes melanoma cells; and plant cells. Hosts for a great variety of expression constructs are well known, and those of skill will be enabled by the present disclosure readily to select a host for expressing a polypeptides in accordance with this aspect of the present invention. Appropriate culture mediums and conditions for the above-described host cells are known in the art.

Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors available to those of skill in the art.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5- has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The DR3 and DR3-V1 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

DR3-V1 or DR3 polynucleotides and polypeptides may be used in accordance with the present invention for a variety of applications, particularly those that make use of the chemical and biological properties of DR3. Among these are applications in treatment of tumors, resistance to parasites, bacteria and viruses, to induce proliferation of T-cells, endothelial cells and certain hematopoietic cells, to treat restenosis, graft vs. host disease, to regulate anti-viral responses and to prevent certain autoimmune diseases after stimulation of DR3 by an agonist. Additional applications relate to diagnosis and to treatment of disorders of cells, tissues and organisms. These aspects of the invention are discussed further below.

DR3 Polypeptides and Fragments

The invention further provides an isolated DR3-V1 or DR3 polypeptide having the amino acid sequence shown in FIGS. 1A–1C [SEQ ID NO:2] and FIGS. 2A–2B[SEQ ID NO:4], respectively, or a fragment thereof It will be recognized in the art that some amino acid sequence of DR3-V1 or DR3 can be varied without significant effect of the structure or function of the protein. If such differences in sequence are contemplated, it should be remembered that there will be critical areas on the protein which determine activity. Such areas will usually comprise residues which make up the ligand binding site or the death domain, or which form tertiary structures which affect these domains.

Thus, the invention further includes variations of the DR3-V1 or DR3 protein which show substantial DR3 protein activity or which include regions of DR3-V1 or DR3 such as the protein fragments discussed below. Such mutants include deletions, insertions, inversions, repeats, and type substitutions. As indicated above, guidance concerning which amino acid changes are likely to be phenotypically silent can be found in J. U. Bowie et al., *Science* 247: 1306–1310 (1990).

Of particular interest are substitutions of charged amino acids with another charged amino acid and with neutral or negatively charged amino acids. The latter results in proteins with reduced positive charge to improve the characteristics of the DR3-V1 or DR3 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the DR3-V1 or DR3 receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

| Conservative Amino Acid Substitutions. | |
|---|---|
| Aromatic | Phenylalanine |
| | Tryptophan |
| | Tyrosine |
| Hydrophobic | Leucine |
| | Isoleucene |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the DR3-V1 or DR3 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form, and preferably are substantially purified. A recombinantly produced version of the DR3-V1 or DR3 polypeptide is substantially purified by the one-step method described in Smith and Johnson, *Gene* 67:31–40 (1988).

The polypeptides of the present invention also include the polypeptide encoded by the deposited cDNA including the leader, the mature polypeptide encoded by the deposited the cDNA minus the leader (i.e., the mature protein), the polypeptide of FIGS. 1A–1C (SEQ ID NO:2) or FIGS. 2A–2B (SEQ ID NO:4) including the leader, the polypeptide of FIGS. 1A–1C (SEQ ID NO:2) or FIGS. 2A–2B (SEQ ID NO:4) minus the leader, the extracellular domain, the transmembrane domain, the intracellular domain, soluble polypeptides comprising all or part of the extracellular and intracelluar domains but lacking the transmembrane domain as well as polypeptides which are at least 80% identical, more preferably at least 90% or 95% identical, still more preferably at least 96%, 97%, 98% or 99% identical to the polypeptide encoded by the deposited cDNA clones, to the polypeptide of FIGS. 1A–1C (SEQ ID NO:2) or FIGS. 2A–2B (SEQ ID NO:4), and also include portions of such polypeptides with at least 30 amino acids and more preferably at least 50 amino acids.

By a polypeptide having an amino acid sequence at least, for example, 95% "identical" to a reference amino acid sequence of a DR3-V1 or DR3 polypeptide is intended that the amino acid sequence of the polypeptide is identical to the reference sequence except that the polypeptide sequence may include up to five amino acid alterations per each 100 amino acids of the reference amino acid of the DR3-V1 or DR3 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A–1C (SEQ ID NO:2), or FIGS. 2A–2B (SEQ ID NO:4) or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The present inventors have discovered that the DR3-V1 polypeptide is a 428 residue protein exhibiting three main structural domains. First, the ligand binding domain was identified within residues from about 36 to about 212 in FIGS. 1A–1C [SEQ ID NO:2]. Second, the transmembrane domain was identified within residues from about 213 to about 235 in FIGS. 1A–1C [SEQ ID NO:2]. Third, the intracellular domain was identified within residues from about 236 to about 428 in FIGS. 1A–1C [SEQ ID NO:2]. Importantly, the intracellular domain includes a death domain at residues from about 353 to about 419. Further preferred fragments of the polypeptide shown in FIGS. 1A–1C [SEQ ID NO:2] include the mature protein from residues about 36 to about 428 and soluble polypeptides comprising all or part of the extracellular and intracellular domains but lacking the transmembrane domain.

Preferred polypeptide fragments of the present invention also include: amino acid residues from about 1 to about 215 of SEQ ID NO:2; amino acid residues from about 30 to about 215 of SEQ ID NO:2; amino acid residues from about 215 to about 240 of SEQ ID NO:2; amino acid residues from about 240 to about 428 of SEQ ID NO:2; and amino acid residues from about 350 to about 420 of SEQ ID NO:2.

The present inventors have also discovered that the DR3 polypeptide is a 417 residue protein exhibiting three main structural domains. First, the ligand binding domain was identified within residues from about 25 to about 201 in FIGS. 2A–2B [SEQ ID NO:4]. Second, the transmembrane domain was identified within residues from about 202 to about 224 in FIGS. 2A–2B [SEQ ID NO:4]. Third, the intracellular domain was identified within residues from about 225 to about 417 in FIGS. 2A–2B [SEQ ID NO:4]. Importantly, the intracellular domain includes a death domain at residues from about 342 to about 408. Further preferred fragments of the polypeptide shown in FIGS. 2A–2B [SEQ ID NO:4] include the mature protein from residues about 25 to about 417 and soluble polypeptides comprising all or part of the extracellular and intracellular domains but lacking the transmembrane domain. As one of skill in the art will recognize, the full length polypeptides encoded by the DR3-V1 and DR3 cDNA differ only in the amino acid sequence of the leader peptide. The first 24 amino acids of the polypeptide shown in FIGS. 1A–1C are replaced by the first 13 amino acids shown in FIGS. 2A–2B but the rest of the amino acid sequence is the same. Thus, both the DR3-V1 cDNA and DR3 cDNA encode an identical mature protein having the same biological activity.

Thus, the invention further provides DR3-V1 or DR3 polypeptides encoded by the deposited cDNA clones including the leader and DR3-V1 or DR3 polypeptide fragments selected from the mature protein, the extracellular domain, the transmembrane domain, the intracellular domain, and the death domain.

In another aspect, the invention provides a peptide or polypeptide comprising an epitope-bearing portion of a polypeptide described herein. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, J. G. Sutcliffe et al., "Antibodies that react with predetermined sites on proteins," *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention.

Non-limiting examples of antigenic polypeptides or peptides that can be used to generate DR3-specific antibodies include: a polypeptide comprising amino acid residues from about 1 to about 22 in FIGS. 1A–1C (SEQ ID NO:2); a polypeptide comprising amino acid residues from about 33 to about 56 in FIGS. 1A–1C (SEQ ID NO:2); a polypeptide comprising amino acid residues from about 59 to about 82 in FIGS. 1A–1C (SEQ ID NO:2); a polypeptide comprising amino acid residues from about 95 to about 112 in FIGS. 1A–1C (SEQ ID NO:2); a polypeptide comprising amino acid residues from about 122 to about 133 in FIGS. 1A–1C (SEQ ID NO:2); a polypeptide comprising amino acid residues from about 161 to about 177 in FIGS. 1A–1C (SEQ ID NO:2); a polypeptide comprising amino acid residues from about 179 to about 190 in FIGS. 1A–1C (SEQ ID NO:2); and a polypeptide comprising amino acid residues from about 196 to about 205 in FIGS. 1A–1C (SEQ ID NO:2). In addition, antigenic polypeptides or peptides include polypeptides comprising the amino acid residues that are the corresponding residues to those polypeptides of DR3-V1 disclosed above. As indicated above, the inventors have determined that the above polypeptide fragments are antigenic regions of the DR3-V1 and DR3 protein.

The epitope-bearing peptides and polypeptides of the invention may be produced by any conventional means. R. A. Houghten, "General method for the rapid solid-phase synthesis of large numbers of peptides: specificity of antigen-antibody interaction at the level of individual amino acids," *Proc. Natl. Acad Sci. USA* 82:5131–5135 (1985). This "Simultaneous Multiple Peptide Synthesis (SMPS)" process is further described in U.S. Pat. No. 4,631,211 to Houghten et al. (1986).

As one of skill in the art will appreciate, DR3-V1 or DR3 polypeptides of the present invention, and the epitope-bearing fragments thereof, described above, can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric DR3-V1 or DR3 protein or protein fragment alone (Fountoulakis et al., *J Biochem* 270:3958–3964 (1995)).

Polypeptide Assays

The present invention also relates to diagnostic assays such as quantitative and diagnostic assays for detecting levels of DR3-V1 or DR3 protein, or the soluble form thereof, in cells and tissues, including determination of normal and abnormal levels. Thus, for instance, a diagnostic assay in accordance with the invention for detecting over-expression of DR3-V1 or DR3, or soluble form thereof, compared to normal control tissue samples may be used to detect the presence of tumors, for example. Assay techniques that can be used to determine levels of a protein, such as an DR3 protein of the present invention, or a soluble form thereof, in a sample derived from a host are well-known to those of skill in the art. Such assay methods include radioimmunoassays, competitive-binding assays, Western Blot analysis and ELISA assays.

Assaying DR3-V1 or DR3 protein levels in a biological sample can occur using any art-known method. Preferred for assaying DR3-V1 or DR3 protein levels in a biological sample are antibody-based techniques. For example, DR3-V1 or DR3 protein expression in tissues can be studied with classical immunohistological methods. M. Jalkanen et al., *J. Cell. Biol.* 101:976–985 (1985); M. Jalkanen et al., *J. Cell. Biol.* 105:3087–3096 (1987).

Other antibody-based methods useful for detecting DR3-V1 or DR3 protein gene expression include immunoassays, such as the enzyme linked immunosorbent assay (ELISA) and the radioimmunoassay (RIA).

Suitable labels are known in the art and include enzyme labels, such as glucose oxidase, radioisotopes, such as iodine ($^{125}$I, $^{121}$I, carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (D. V. Goeddel et al., "Tumor Necrosis Factors: Gene Structure and Biological Activities," *Symp. Quant. Biol.* 51:597–609 (1986), Cold Spring Harbor, B. Beutler and A. Cerani, *Annu. Rev. Biochem.* 57:505–518 (1988); L. J. Old, *Sci. Am.* 258:59–75 (1988); W. Fiers, *FEBS Lett.* 285:199–224 (1991)). The TNF-family ligands induce such various cellular responses by binding to TNF-family receptors, including the DR3-V1 or DR3 of the present invention. Cells which express the DR3-V1 or DR3 polypeptide and are believed to have a potent cellular response to DR3-V1 or DR3 ligands include lymphocytes, fibroblasts, macrophages, synovial cells, activated T-cells, lymphoblasts and epithelial cells. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis. Apoptosis-programmed cell death is a physiological mechanism involved in the deletion of peripheral T lymphocytes of the immune system, and its dysregulation can lead to a number of different pathogenic processes (J. C. Ameisen, *AXDS* 8:1197–1213 (1994); P. H. Krammer et al., *Curr. Opin. Immunol.* 6:279–289 (1994)).

Diseases associated with increased cell survival, or the inhibition of apoptosis, include cancers (such as follicular lymphomas, carcinomas with p53 mutations, and hormone-dependent tumors, such as breast cancer, prostrate cancer, Kaposi's sarcoma and ovarian cancer); autoimmune disorders (such as systemic lupus erythematosus, immune-related glomerulonephritis, and rheumatoid arthritis) and viral infections (such as herpes viruses, pox viruses and adenoviruses), information graft versus host disease, acute graft rejection, and chronic graft rejection. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia, and anorexia.

Thus, in one aspect, the present invention is directed to a method for enhancing apoptosis induced by a TN-family ligand, which involves administering to a cell which expresses the DR3-V1 or DR3 polypeptide an effective amount of DR3-V1 or DR3 ligand, analog or an agonist capable of increasing DR3-V1 or DR3 mediated signaling. Preferably, DR3-V1 or DR3 mediated signaling is increased to treat a disease wherein decreased apoptosis or decreased cytokine and adhesion molecule expression is exhibited. An agonist can include soluble forms of DR3-V1 or DR3 and monoclonal antibodies directed against the DR3-V1 or DR3 polypeptide.

In a further aspect, the present invention is directed to a method for inhibiting apoptosis induced by a TNF-family ligand, which involves administering to a cell which expresses the, DR3-V1 or DR3 polypeptide an effective amount of an antagonist capable of decreasing DR3-V1 or DR3 mediated signaling. Preferably, DR3-V1 or DR3 mediated signaling is decreased to treat a disease wherein increased apoptosis or NFkB expression is exhibited. An antagonist can include soluble forms of DR3-V1 or DR3 and monoclonal antibodies directed against the DR3-V1 or DR3 polypeptide.

By "agonist" is intended naturally occurring and synthetic compounds capable of enhancing or potentiating apoptosis. By "antagonist" is intended naturally occurring and synthetic compounds capable of inhibiting apoptosis. Whether any candidate "agonist" or "antagonist" of the present invention can enhance or inhibit apoptosis can be determined using art-known TNF-family ligand/receptor cellular response assays, including those described in more detail below.

One such screening procedure involves the use of melanophores which are transfected to express the receptor of the present invention. Such a screening technique is described in PCT WO 92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation, for example, as described in Science 246:181–296 (October 1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing in cells a construct wherein the receptor is linked to a phospholipase C or D. Such cells include endothelial cells, smooth muscle cells, embryonic kidney cells, etc. The screening may be accomplished as hereinabove described by detecting activation of the receptor or inhibition of activation of the receptor from the phospholipase signal.

Another method involves screening for compounds which inhibit activation of the receptor polypeptide of the present invention antagonists by determining inhibition of binding of labeled ligand to cells which have the receptor on the surface thereof Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonist and antagonist of the present invention are described in L. A. Tartaglia and D. V. Goeddel, *J. Biol. Chem.* 267:43044307(1992).

Thus, in a further aspect, a screening method is provided for determining whether a candidate agonist or antagonist is capable of enhancing or inhibiting a cellular response to a TNF-family ligand. The method involves contacting cells which express the DR3-V1 or DR3 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the DR3-V1 or DR3 polypeptide can be contacted with either an endogenous or exogenously administered TNF-family ligand.

Agonist according to the present invention include naturally occurring and synthetic compounds such as, for example, TNF family ligand peptide fragments, transforming growth factor β, neurotransmitters (such as glutamate, dopamine, N-methyl-D-aspartate), tumor suppressors (p53), cytolytic T cells and antimetabolites. Preferred agonist include chemotherapeutic drugs such as, for example, cisplatin, doxorubicin, bleomycin, cytosine arabinoside, nitrogen mustard, methotrexate and vincristine. Others include ethanol and β-amyloid peptide (*Science* 267:1457–1458 (1995)). Further preferred agonists include polyclonal and monoclonal antibodies raised against the DR3-V1 or DR3 polypeptide, or a fragment thereof Such agonist antibodies raised against a TNF-family receptor are disclosed in L. A. Tartaglia et al., *Proc. Natl. Acad Sci. USA* 88:9292–9296 (1991); and L. A. Tartaglia and D. V. Goeddel, supra See, also, PCT Application WO 94/09137.

Antagonist according to the present invention include naturally occurring and synthetic compounds such as, for example, the CD40 ligand, neutral amino acids, zinc, estrogen, androgens, viral genes (such as Adenovirus ElB, Baculovirus p35 and IAP, Cowpox virus crmA, Epstein-Barr virus BHRF1, LMP-1, African swine fever virus LMW5-HL, and Herpesvirus yl 34.5), calpain inhibitors, cysteine protease inhibitors, and tumor promoters (such as PMA, Phenobarbital, and α-Hexachlorocyclohexane).

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression*, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

Further antagonist according to the present invention include soluble forms of DR3-V1 or DR3, i.e., DR3-V1 or DR3 fragments that include the ligand binding domain from the extracellular region of the full length receptor. Such soluble forms of the receptor, which may be naturally occurring or synthetic, antagonize DR3-V1 or DR3 mediated signaling by competing with the cell surface DR3-V1 or DR3 for binding to TNF-family ligands. Thus, soluble forms of the receptor that include the ligand binding domain are novel cytokines capable of inhibiting apoptosis induced by TNF-family ligands. These are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (D. P. Hughes and I. N. Crispe, *J. Exp. Med* 182:1395–1401 (1995)).

The experiments set forth in Examples 6 and 7 demonstrate that DR3 is a death domain-containing molecule capable of triggering both apoptosis and NF-kB activation, two pathways dominant in the regulation of the immune system. The experiments also demonstrate the internal signal transduction machinery of this novel cell death receptor. In addition, the experiments set forth below demonstrate that DR3-induced apoptosis was blocked by the inhibitors of ICE-like proteases, CrmA and z-VAD-fink. Importantly, apoptosis induced by DR3 was also blocked by dominant negative versions of FADD (FADD-DN) or FLICE (FLICE-DN/MACHa1C360S), which were previously shown to inhibit death signaling by Fas/APO-1 and TNFR-1. Thus, inhibitors of ICE-like proteases, FADD-DN and FLICE-DN/MACHa1C360S could also be used as antagonists for DR3 activity.

The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med* 24:316–325 (1983)).

Antibodies according to the present invention may be prepared by any of a variety of methods using DR3-V1 or DR3 immunogens of the present invention. As indicated, such DR3-V1 or DR3 immunogens include the full-length DR3-V1 or DR3 polypeptide (which may or may not include the leader sequence) and DR3-V1 or DR3 polypeptide fragments such as the ligand binding domain, the transmembrane domain, the intracellular domain and the death domain.

Proteins and other compounds which bind the DR3-V1 or DR3 domains are also candidate agonist and antagonist according to the present invention. Such binding compounds can be "captured" using the yeast two-hybrid system (Fields and Song, *Nature* 340:245–246 (1989)). A modified version of the yeast two-hybrid system has been described by Roger Brent and his colleagues (J. Gyuris et al., *Cell* 75:791–803 (1993); A.S. Zervos et al., *Cell* 72:223–232 (1993)). Preferably, the yeast two-hybrid system is used according to the present invention to capture compounds which bind to either the DR3-V1 or DR3 ligand binding domain or to the DR3-V1 or DR3 intracellular domain. Such compounds are good candidate agonist and antagonist of the present invention.

By a "TNF-family ligand" is intended naturally occuring, recombinant, and synthetic ligands that are capable of binding to a member of the TNF receptor family and inducing the ligand/receptor signaling pathway. Members of the TNF ligand family include, but are not limited to, the DR3-V1 or DR3 ligand, TNF-α, lymphdtoxin-α (LTα, also known as TNF-β), LT-β (found in complex heterotrimer LT-α2-β), FasL, CD40, CD27, CD30, 4-lBB, OX40 and nerve growth factor (NGF).

Representative therapeutic applications of the present invention are discussed in-more detail below. The state of immunodeficiency that defines AIDS is secondary to a decrease in the number and function of CD4$^+$ T-lymphocytes. Recent reports estimate the daily loss of CD4$^+$ T cells to be between 3.5×10$^7$ and 2×10$^9$ cells (X. Wei et al., *Nature* 373:117–122 (1995)). One cause of CD4$^+$ T cell depletion in the setting of HIV infection is believed to be HIV-induced apoptosis. Indeed, HIV-induced apoptotic cell death has been demonstrated not only in vitro but also, more importantly, in infected individuals (J. C. Ameisen, *AIDS* 8:1197–1213 (1994); T. H. Finkel and N. K. Banda, *Curr. Opin. Immunol.* 6:605–615(1995); C. A. Muro-Cacho et al., *J. Immunol.* 154:5555–5566 (1995)). Furthermore, apoptosis and CD4$^+$ T-lymphocyte depletion are tightly correlated in different animal models of AIDS (T. Brunner et al., *Nature* 373:441–444 (1995); M. L. Gougeon et al., *AIDS Res. Hum. Retroviruses* 9:553–563 (1993)), and apoptosis is not observed in those animal models in which viral replication does not result in AIDS. Id. Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (A. D. Badley et al., *J. Virol.* 70:199–206 (1996)). Further, the TNF-family ligand was detectable in uninfected macrophages and its expression was upregulated following HIV infection resulting in selective killing of uninfected CD4 T-lymphocytes. Id. Thus, by the invention, a method for treating HIV$^+$ individuals is provided which involves administering an antagonist of the present invention to reduce selective killing of CD4 T-lymphocytes. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. Agonist of the present invention are able to suppress the immune response to both allografts and xenografts because lymphocytes activated and differentiated into effector cells will express the DR3-V1 or DR3 polypeptide, and thereby are susceptible to compounds which enhance apoptosis. Thus, the present invention further provides a method for creating immune privileged tissues. Antagonist of the invention can further be used in the treatment of Inflammatory Bowel-Disease.

DR3, like TNFR1, also activates the NF-kB transcription factor, which is very closely associated with the stimulation of cytokine (e.g., IL-8) and adhesion molecule (e.g., ELAM) transcription. Hence, like TNF, the ligand (or agonist) for DR3 and DR3-V1 may in some circumstances be proinflammatory, and antagonists may be useful reagents for blocking this response. Thus, DR3 and DR3-V1 antagonists may be useful for treating inflammatory diseases, such as rheumatoid arthritis, osteoarthritis, psoriasis, septicemia, and inflammatory bowel disease.

In addition, due to lymphoblast expression of DR3, soluble DR3, agonist or antagonist mABs may be used to treat this form of cancer. Further, soluble DR3 or neutralizing mABs may be used to treat various chronic and acute forms of inflammation such as rheumatoid arthritis, osteoarthritis, psoriasis, septicemia, and inflammatory bowel disease.

Modes of Administration

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit DR3-V1 or DR3 mediated apoptosis. Of course, where apoptosis is to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients.

It will be understood that, when administered to a human patient, the total daily usage of the compounds and compositions of the present invention will be decided by the attending physician within the scope of sound medical judgement. The specific therapeutically effective dose level for any particular patient will depend upon factors well known in the medical arts.

As a general proposition, the total pharmaceutically effective amount of DDCR polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the DDCR agonists or antagonists is typically administered at a dose rate of about 1 μg/kg/hour to about 50 μg/kg/hour, either by 14 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

Pharmaceutical compositions are provided comprising an agonist or antagonist and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. Importantly, by co-administering an agonist and a TNF-family ligand, clinical side effects can be reduced by using lower doses of both the ligand and the agonist. It will be understood that the agonist can be "co-administered" either before, after, or simultaneously with the TNF-family ligand, depending on the exigencies of a particular therapeutic application. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

In addition to soluble DR3-V1 or DR3 polypeptides, DR3-V1 or DR3 polypeptide containing the transmembrane region can also be used when appropriately solubilized by including detergents, such as CHAPS or NP40, with buffer.

EXAMPLE 1

Expression and Purification in *E. coli*

The DNA sequence encoding the mature DR3-V1 protein in the deposited cDNA clone (ATCC No. 97456) is amplified using PCR oligonucleotide primers specific to the amino terminal sequences of the DR3-V1 protein and to vector sequences 3' to the gene. Additional nucleotides containing restriction sites to facilitate cloning are added to the 5' and 3' sequences respectively.

The following primers are used for expression of DR3 extracellular domain in E. coli 5' primer 5'-GCGCCATGGGGGCCCGGCGGCAG-3' (SEQ ID NO:7) contains an NcoI site and 15 nucleotide starting from 290 nucleotide to 304 FIGS. 1A–1C. 3' primer 5'-GCGAAGCTTCTAGGACCCAGAACATCTGCC-3' (SEQ ID NO:8) contains a HindIII site, a stop codon and 18 nucleotides complimentary to nucleotide from 822 to 840 in FIGS. 1A–1C. Vector is pQE60. The protein is not tagged.

The restriction sites are convenient to restriction enzyme sites in the bacterial expression vector pQE60, which are used for bacterial expression in these examples. (Qiagen, Inc. 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS").

The amplified DR3-V1 DNA and the vector pQE60 both are digested with Nco I and HindIII and the digested DNAs are then ligated together. Insertion of the DDCR protein DNA into the restricted pQE60 vector places the DR3-V1 protein coding region downstream of and operably linked to the vector's IPTG-inducible promoter and in-frame with an initiating AUG appropriately positioned for translation of DR3-V1 protein.

The ligation mixture is transformed into competent *E. coli* cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan$^r$"), is used in carrying out the illustrative example described herein. This strain, which is only one of many that are suitable for expressing DR3-V1 protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 µg/ml) and kanamycin (25 µg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2× phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2X PBS at a concentration of 95 µg/ml.

EXAMPLE 2

Expression in Mammalian Cells

Most of the vectors used for the transient expression of a given gene sequence in mammalian cells carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI, and the early promoter of the cytomegalovirus (CMV). However, also cellular signals can be used (e.g., human actin, promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC67109). Mammalian host cells that could be used include, human Hela, 283, H9 and Jurkat cells, mouse NIH3T3 and C127 cells, Cos 1, Cos 7, and CV1 African green monkey cells, quail QC1–3 cells, mouse L cells, and Chinese hamster ovary (CHO) cells.

Alternatively, a gene of interest can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Using this marker, the mammalian cells are grown in increasing amounts of methotrexate for selection and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology* 438:44701 (March 1985)), plus a fragment of the CMV-enhancer (Boshart et al., *Cell* 41:521–530 (1985)). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

EXAMPLE 2A

Expression of Extracellular Soluble Domain of DR3-V1 and DR3 in COS Cells

The expression plasmid, pDR3-V1 HA, is made by cloning a cDNA encoding DR3-V1 (ATCC No. 97456) into the expression vector pcDNAI/Amp (which can be obtained from Invitrogen, Inc.). Expression plasmid, pDR3 HA, is made by cloning a cDNA encoding DR3 (ATCC No. 97757) into the expression vector pcDNAI/Amp.

The expression vector pcDNAI/amp contains: (1) an *E. coil* origin of replication effective for propagation in *E. coli* and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire DR3-V1 or Dr3 precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37:767 (1984). The fusion of the HA tag to the target protein allows easy detection of the recombinant protein with an antibody that recognizes the HA epitope.

The plasmid construction strategy is as follows:

The DR3-V1 or DR3 cDNA of the deposit clone is amplified using primers that contained convenient restriction sites, much as described above regarding the construction of expression vectors for expression of DR3-V1 or DR3 in E. coil and S. fugiperda.

To facilitate detection, purification and characterization of the expressed DR3-V1 or DR3, one of the primers contains a hemagglutinin tag ("HA tag") as described above.

Suitable primers for DR3-V1 include the following, which are used in this example, the 5' primer, 5' CGC GGATCCGCCATCATGGAGGAGACGCAGCAG 3' (SEQ ID NO:9) contains the underlined BamHI site, an ATG start codon and 5 codons thereafter.

Suitable primers for DR3 include the following, which are used in this example, the 5' primer, 5' CGC GGATCCGCCATCATGGAGCAGCGGCCGCGG 3' (SEQ ID NO:10) contains the underlined BamHI site, an ATG start codon and 5 codons thereafter.

The 3' primer for both DR3 and DR3-V1, containing the underlined XbaI site, stop codon, hemagglutinin tag and last 14 nucleotide of 3' coding sequence (at the 3' end) has the following sequence: 5'GCG TCTAGATCAAAGCGTAGTCTGGGACGTCGTATGGG TACGGGCCGCGCTGCA 3' (SEQ ID NO:11).

The PCR amplified DNA fragment and the vector, pcDNAI/Amp, are digested with BamHI and XbaI and then ligated. The ligation mixture is transformed into E. coli strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the DR3-V1 or DR3-encoding fragment.

For expression of recombinant DR3-V1 or DR3, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989).

Cells are incubated under conditions for expression of DR3-V1 or DR3 by the vector.

Expression of the DR3-V1 HA fusion protein or the DR3 HA fusion protein is detected by radiolabelling and immunoprecipitation, using methods described in, for example Harlow et al., *Antibodies: a Laboratory Manual*, 2nd Ed., Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and then lysed with detergent-containing RIPA buffer: 150 mM NaCl, 1% NP-40, 0.1% SDS, 1% NP-40, 0.5% DOC, 50 mM TRIS, pH 7.5, as described by Wilson et al cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

EXAMPLE 2B

Expression and Purification of Human DR3-V1 and DR3 using the CHO Expression System The vector pC1 is used for the expression of DR3-V1 or DR3 (ATCC No. 97456 or ATCC No. 97757, respectively) protein. Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., F. W. Alt et al. *J Biol. Chem.* 253:1357–1370 (1978); J. L. Hamlin and C. Ma, *Biochem. et Biophys. Acta*, 1097:107–143 (1990); M. J. Page and M. A. Sydenham, *Biotechnology* 9:64–68 (1991)). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rous Sarcoma Virus (Cullen et al., *Molecular and Cellular Biology* 5:438447 (March 1985)), plus a fragment isolated from the enhancer of the immediate early gene of human cytomegalovirus (CMV) (Boshart et al., *Cell* 41:521–530 (1985)). Downstream from the promoter are the following single restriction enzyme cleavage sites that allow the integration of the genes: BamHI followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding DR3-V1 or DR3 in the deposited cDNA clones are amplified using PCR oligonucleotide primers specific to the amino acid carboxyl terminal sequence of the DR3-V1 or DR3 protein and to vector sequences 3' to the gene. Additional nucleotides containing restriction sites to facilitate cloning are added to the 5' and 3' sequences respectively.

The 5' oligonucleotide primer for DR3-V1 has the sequence 5' CGC GGATCCGCCATCATGGAGGAGACGCAGCAG 3' (SEQ ID NO:12) containing the underlined BamHI restriction site, which encodes a start AUG, followed by the Kozak sequence ad 18 nucleotides of the DR3-V1 coding sequence set out in FIGS. 1A–1C beginning with the 1st base of the ATG codon.

The 5' oligonucleotide primer for DR3 has the sequence 5' CGCGGATCCGCCATCATGGAGCAGCGGCCGCGG 3' (SEQ ID NO:13) containing the underlined BamHI restriction site, which encodes a start AUG, followed by the Kozak sequence and 18 nucleotides of the DR3 coding sequence set out in FIGS. 2A–2B beginning with the first base of the ATG codon.

The 3' primer for both DR3 and DR3-V1 has the sequence 5' CGC<u>GGATCC</u>TCACGGGCCGCGCTGCA 3' (SEQ ID NO:14) containing the underlined BamHI restriction site followed by 17 nucleotides complementary to the last 14 nucleotides of the DR3-V1 or DR3 coding sequence set out in FIGS. 1A–1C or FIGS. 2A–2B, respectively, plus the stop codon.

The restrictions sites are convenient to restriction enzyme sites in the CHO expression vectors pC1.

The amplified DR3 or DR3-V1 DNA and the vector pC1 both are digested with BamHI and the digested DNAs then ligated together. Insertion of the DR3-V1 or DR3 DNA into the BamHI restricted vector placed the DR3-V1 or DR3 coding region downstream of and operably linked to the vector's promoter. The sequence of the inserted gene is confirmed by DNA sequencing.

Transfection of CHO-DHFR-cells

Chinese hamster ovary cells lacking an active DHFR enzyme are used for transfection. 5 µg of the expression plasmid C1 are cotransfected with 0.5 µg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25 nM 50 nM 100 nM, 200 nM 400 nM). Clones growing at the highest concentrations of methotrexate are then transferred to new 6-well plates containing even higher concentrations of methotrexate (500 nM, 1 µM, 2 µM, 5 µM). The same procedure is repeated until clones grow at a concentration of 100 µM.

The expression of the desired gene product is analyzed by Western blot analysis and SDS-PAGE.

EXAMPLE 3

Cloning and Expression of the Soluble Extracellular Domain of DR3-V1 and DR3 in a Baculovirus Expression System The cDNA sequence encoding the soluble extracellular domain of DR3-V1 or DR3 protein in the deposited clone (ATCC No. 97456 or ATCC No. 97757, respectively) is amplified using PCR oligonucleotide primers corresponding to the 5' and 3' sequences of the gene:

The 5' primer for DR3-V1 has the sequence 5° CGC <u>GGATCC</u>GCCATCATGGAGGAGACGCAGCAG 3' (SEQ ID NO:15) containing the underlined BamHI restriction enzyme site followed by a Kozak sequence and a number of bases of the sequence of DR3-V1 of FIGS. 1A–1C. Inserted into an expression vector, as described below, the 5' end of the amplified fragment encoding DR3-V1 provides an efficient signal peptide. An efficient signal for initiation of translation in eukaryotic cells, as described by M. Kozak, J. Mol. Biol. 196:947–950 (1987) is appropriately located in the vector portion of the construct.

The 5' primer for DR3 has the sequence 5° CGC <u>GGATCC</u>GCCATCATGGAGCAGCGGCCGCGG 3' (SEQ ID NO:16) containing the underlined BamHI restriction enzyme site followed by a Kozak sequence and a number of bases of the sequence of DR3 of FIGS. 2A–2B. Inserted into an expression vector, as described below, the 5' end of the amplified fragment encoding DR3 provides an efficient signal peptide. An efficient signal for initiation of translation in eukaryotic cells, as described by M. Kozak, J. Mol. Biol. 196:947–950 (1987) is appropriately located in the vector portion of the construct.

The 3' primer for both DR3 and DR3-V1 has the sequence 5' GCG<u>AGATCT</u>AGTCTGGACCC AGAACATCTGC-CTCC 3' (SEQ ID NO:17) containing the underlined XbaI restriction followed by nucleotides complementary to the DR3-V1 or DR3 nucleotide sequence set out in FIGS. 1A–1C or FIGS. 2A–2B, respectively, followed by the stop codon.

The amplified fragment is isolated from a 1% agarose gel using a commercially available kit ("Geneclean," BIO 101 Inc., La Jolla, Calif.) The fragment then is digested with BamHI and Asp718 and again is purified on a 1% agarose gel. This fragment is designated herein F2.

The vector pA2 is used to express the DR3-V1 or DR3 protein in the baculovirus expression system, using standard methods, such as those described in Summers et al., *A Manual of Methods for Baculovirus Vectors and Insect Cell Culture Procedures*, Texas Agricultural Experimental Station Bulletin No. 1555 (1987). This expression vector contains the strong polyhedron promoter of the Autograph californica nuclear polyhedrosis virus (ACMNPV) followed by convenient restriction sites. For an easy selection of recombinant virus the betagalactosidase gene from *E. coli* is inserted in the same orientation as the polyhedron promoter and is followed by the polyadenylation signal of the polyhedron gene. The polyhedron sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170:31–39 (1989), among others.

The plasmid is digested with the restriction enzymes BamHI and XbaI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human DDCR gene by digesting DNA from individual colonies using BamHI and XbaI and then analyzing the digestion product by gel electrophoresis. The sequence of the cloned fragment is confirmed by DNA sequencing. This plasmid is designated herein pBac DR3-V1 or pBac DR3.

5 µg of the plasmid pBac DR3-V1 or pBac DR3 is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 µg of BaculoGold™ virus DNA and 5 µg of the plasmid pBac DR3-V1 are mixed in a sterile well of a microliter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted DR3-V1 or DR3 is identified by DNA analysis including restriction mapping and sequencing. This is designated herein as V-DR3-V1 or V-DR3.

Sf9 cells are grown in Grace's medium supplemented with 10% heat-inactivated FBS. The cells are infected with the recombinant baculovirus V- DR3-V1 at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 gCi of $^{35}$S-methionine and 5 µCi $^{35}$S cysteine (available from Amersham) are added. The cells are further incubated for 16 hours and then they are harvested by centrifugation, lysed and the labeled proteins are visualized by SDS-PAGE and autoradiography.

EXAMPLE 4

A. Tissue Distribution of DR3-V1 Gene Expression

Northern blot analysis is carried out to examine DR3-V1 gene (ATCC No. 97456) expression in human tissues, using methods described by, among others, Sambrook et al., cited above. A cDNA probe containing the entire nucleotide sequence of the DR3-V1 protein (SEQ ID NO:1) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for DR3-V1 mRNA.

Multiple Tissue Northern (MTN) blots containing various human tissues (H) or human immune system tissues (IM) are obtained from Clontech and are examined with labeled probe using ExpressHyb™ hybridization solution (Clontech) according to manufacturer's protocol number PT 1190-1. Following hybridization and washing, the blots are mounted and exposed to film at −70° C. overnight, and films developed according to standard procedures Expression of DR3-V1 was detected in tissues enriched in lymphocytes including peripheral blood leukocytes (PBLs), thymus, spleen, colon, and small intestine. DR3-V1 expression appears to be restricted to lymphocyte compartments, it can be envisaged that DR3-V1 plays a role in lymphocyte homeostasis.

B. Tissue Distribution of DR3 Gene Expression

Northern blot analysis is carried out to examine DR3 gene (ATCC No. 97757) expression in human tissues, using methods described by, among others, Sambrook et al., cited above. A cDNA probe containing the entire nucleotide sequence of the DR3 protein (SEQ ID NO:3) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for DR3 mRNA.

Multiple Tissue Northern (MTN) blots containing various human tissues (H) or human immune system tissues (IM) are obtained from Clontech and are examined with labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

Expression of DR3 was detected in tissues enriched in lymphocytes including peripheral blood leukocytes (PBLs), thymus, spleen, colon, and small intestine. By contrast, TNFR-1 is ubiquitously expressed and Fas/APO-1 is expressed in lymphocytes, liver, heart, lung, kidney, and ovary (Watanabae-Fukunaga et al., *J. Immunol* 148:1274–9 (1992)).

DR3 expression appears to be restricted to lymphocyte compartments, it can be envisaged that DR3 plays a role in lymphocyte homeostasis.

C. Northern Blot Analysis of DR3 in Various Cell Lines

Methods

Cells

Unless stated otherwise, cell lines were obtained from the American Type Culture Collection (Manassas, Va.). The myeloid (Koeffler et al. (1980); Koeffier (1983); Harris and Ralph (1985); and Tucker et al. (1987)) and B-cell lines (Jonak et al. (1922)) studied represent cell types at different stages of the differentiation pathway. KG1a and PLB 985 cells (Tucker et al. (1987)) were obtained from H. P. Koeffler (UCLA School of Medicine). BJA-B was from Z. Jonak (SmithKline Beecham). TF274, a stromal cell line exhibiting osteoblastic features, was generated from the bone marrow of a healthy male donor (Z. Jonak and K. B. Tan, unpublished). Primary carotid artery endothelial cells were purchased from Clonetics Corp. (San Diego, Calif.) and monocytes were prepared by differential centrifugation of peripheral blood mononuclear cells and adhesion to tissue culture dish. CD19+, CD4+and CD8+cells (>90% pure) were isolated with cell type specific immunomagnetic beads (Drynal, Lake Success, N.Y.).

RNA Analysis

Total RNA of adult tissues were purchased from Clonetech (Palo Alto, Calif.). Total RNA was extracted from cell lines (in exponential growth phase) and primary cells with TriReagent (Molecular Research Center, Inc., Cincinnati, Ohio). 5 to 7.5 µg of total RNA was fractionated in a 1% agarose gel containing formaldehyde cast in a Wide Mini-Sub Cell gel tray (Bio-Rad, Hercules, Calif.) as described (Sambrook, et al.) with slight modifications. The formaldehyde concentration was reduced to 0.5M and the RNA was stained prior to electrophoresis with 100 µg/ml of ethidium bromide that was added to the loading buffer. After electrophoresis with continuous buffer recirculation (60 volts/90 min), the gel was photographed and the RNA was transferred quantitatively to Zeta-probe nylon membrane (Biorad, Hercules, Calif.) by vacuum-blotting with 25 mM NaOH for 90 min. After neutralization for 5–10 min, with 1M Tris-HCl, pH 7.5 containing 3M NaCl, the blots were prehybridized with 50% formamide, 8% dextran sulfate, 6×SSPE, 0.1% SDS and 100 µg/ml of sheared and denatured salmon sperm DNA for at least 30 min at 42° C. cDNA inserts labeled with $^{32}$P-dCTP by random priming (Stratagene, La Jolla, Calif.), were denatured with 0.25M NaOH (10 min at 37° C.) and added to the prehybridization solution. After 24–65 hr at 42° C., the blots were washed under high stringency conditions (Sambrook, et al.) and exposed to X-ray films.

Results

Expression of DR3 was assessed by Northern blot in the following cell lines: TF274 (bone marrow stromal); MG63, TE85 (osteosarcoma); K562 (erythroid); KG1a, KG1, PLB985, HL60, U937, TNHP-1 (myeloid); REH, BJAB, Raji, IM-9 (B cell); Sup-T1, Jurkat, H9, Molt-3 (T cell); RL95-2 (endometrial carcinoma); MCF-7 (breast cancer); BE, HT29 (colon cancer); IMR32 (neuroblastoma) and could only be detected in KG1a cells. DR3 expression was detected in several lymphoblast cell lines. In the purified human hematopoietic cell populations, DR3 was weakly expressed in CD19+cells, and more highly expressed in monocytes. However the highest levels were observed in T cells (CD4+or CD8+) upon stimulation with PMA and PHA, indicating that DR3 probably plays a role in the regulation of T cell activation.

EXAMPLE 5

Intracellular Signaling Molecules used by DR3 Protein

In vitro and in vivo binding studies were undertaken to investigate DR3 signaling pathways. Since DR3 contains a death domain, the inventors postulated that DR3, like TNFR-1 and Fas/APO-1, may transduce signals by recruiting death domain-containing adapter molecules (DAMs) such as FADD, TRADD, and RIP.

Experimental Design

In vitro binding experiments were performed as described previously (A. M. Chinnaiyan et al., Cell 81: 505–12 (1995); M. P. Boldin et al., J Biol Chem 270: 7795–8 (1995); F. C. Kischkel et al., EMBO 14: 5579–5588 (1995)). Briefly, the cytoplasmic domains of DR3 (amino acid residues 215–393 (FIGS. 2A–2B)) and the death domain mutant ΔDR3 (amino acid residues 215–321 (FIGS. 2A–2B)) were amplified by PCR using appropriate templates and primers into pGSTag. pGSTag and pGSTag-TNFR-1 were described previously (A. M. Chinnaiyan et al., Cell 81: 505–12 (1995); M. P. Boldin et al., J Biol Chem 270: 7795–8 (1995); F. C. Kischkel et al., EMBO 14: 5579–5588 (1995)). GST and GST fusion proteins were prepared from E.coli strain BL21 (DE3)pLysS using standard published procedures and the recombinant proteins immobilized onto glutathione-agarose beads. $^{35}$S-Labeled FADD, RIP and TRADD were prepared by in vitro transcription-translation using the TNT or T7 or SP6-coupled reticulocyte lysate system from Promega according to manufacturer's instructions, using pcDNA3 AU1-FADD (A. M. Chinnaiyan et al, Cell 81: 505–12 (1995); M. P. Boldin et al., J Biol Chem 270: 7795–8 (1995); F. C. Kischkel et al., EMBO 14: 5579–5588 (1995)), pRK myc-TRADD (H. Hsu et al., Cell 81: 495–504 (1995)), or pRK myc-RIP (H. Hsu et al., Immunity 4: 387–396 (1996)) as template. Following translation, equal amounts of total $^{35}$S-labeled reticulocyte lysate were diluted into 150 µl GST binding buffer (50 mM Tris, pH 7.6, 120 mM NaCl, 1% NP-40) and incubated for 2 hrs. at 4° C. with the various GST fusion proteins complexed to beads, following the beads were pelleted by plus centrifugation, washed three times in GST buffer, boiled in SDS-sample buffer and resolved on a 12.5% SDS-PAGE. Bound proteins were visualized following autoradioraphy at −80° C. In vitro translated $^{35}$S-labeled RIP, TRADD and FADD were incubated with glutathione beads containing GST alone or GST fusions of the cytoplasmic domain of Fas, TNFR-1,DR3 (215–393), or DDR3 (215–321). After the beads were washed, retained proteins were analyzed by SDS-PAGE and autoradiography. The gel was Coomassie stained to monitor equivalency of loading.

To demonstrate the association of DR3 and TRADD in vivo, constructs encoding Flag-TNFR-1 and Flag-ΔTNFR-1 were used. The Flag-TNFR-1 and Flag-ΔTNFR-1 constructs were described elsewhere (A. M. Chinnaiyan et al., J Biol Chem 271: 49614965 (1996)). The constructs encoding Flag-TNFR-1 and Flag-ΔTNFR-1 were described elsewhere (A. M. Chinnaiyan et al., J Biol Chem 271: 4961–4965 (1996)). To facilitate epitope tagging, DR3 and ΔDR3 (1-321) were cloned into the 1131 Kodak FLAG plasmid (pCMV1FLAG) utilizing the signal peptide provided by the vector. 293 cells (2×10$^6$/100 mm plate) were grown in DMEM media containing 10% heat-inactivated fetal bovine serum containing penicillin G, streptomycin, glutamine, and non-essential amino acids. Cells were transfected using calcium phosphate precipitation with the constructs encoding the indicated proteins in combination with pcDNA3-CrmA (M. Tewari et al., J Biol Chem 270: 3255–60 (1995)) to prevent cell death and thus maintain protein expression. Cells were lysed in 1 ml lysis buffer (50 mM Hepes, 150 mM NaCl, 1 mM EDTA, 1% NP40, and a protease inhibitor cocktail). Lysates were immunoprecipitated with a control monoclonal antibody or anti-Flag antibody for at least 4 hrs, at 4° C. as previously described (AM Chinnaiyan et al., J Biol Chem 271: 49614965 (1996)). The beads were washed with lysis buffer 3×, but in the case of TRADD binding, the NaCl concentration was adjusted to 1M. The precipitates were fractioned on 12.5% SDS-PAGE and transferred to nitrocellulose. Subsequent Western blotting was performed as described elsewhere (H. Hsu et al, Cell 84: 299–308 (1996); A. M. Chinnaiyan et al., J Biol Chem 271, 49614965 (1996)). After 24–32 hours, extracts were prepared and immunoprecipitated with a control monoclonal antibody or anti-Flag monoclonal antibody (IBI Kodak). Western analysis indicated that myc-TRADD and death receptor expression levels were similar in all samples. Coprecipitating myc-TRADD was detected by immunoblotting using an anti-myc HRP conjugated antibody (Boehringer Mannheim).

Results

As an initial screen, in vitro translated radiolabeled DAMs were precipitated with various glutathione S-transferase (GST) fusion proteins immobilized on glutathione-Sepharose beads. As predicted from previous studies (A. M. Chinnaiyan et al., Cell 81: 505–12 (1995); M. P. Boldin et al., J Biol Chem 270: 7795–8 (1995); F. C. Kischkel et al., EMBO 14: 5579–5588 (1995); H. Hsu et al., Cell 81: 495–504 (1995)), FADD associated with the GST-Fas cytoplasmic domain while TRADD associated with the GST-TNFR-1 cytoplasmic domain. In addition, there was a direct, albeit weak, interaction between RIP and GST-TNFR-1. Interestingly, GST-DDCR associated specifically with TRADD, but not FADD or RIP. Furthermore, a truncated death domain mutant of DR3 (GST-DDR3) failed to interact with TRADD. To demonstrate the association of DR3 and TRADD in vivo, 293 cells were transiently transfected with plasmids that direct the synthesis of myc-epitope tagged TRADD (myc-TRADD) and Flag-epitope tagged DR3 (Flag-DR3), Flag-TNFR-1 or mutants. Consistent with the in vitro binding study, TRADD specifically coprecipitated with DR3 and TNFR-1, but not with the death domain mutants, DDR3 and DTNFR-1. Thus, it appears that DR3, like TNFR-1, may activate downstream signaling cascades by virtue of its ability to recruit the adapter molecule TRADD.

Overexpression of TRADD induces apoptosis and NF-kB activation-two of the most important activities signaled by TNFR-1 (H. Hsu et al., supra). Upon oligomerization of TNFR-1 by trimeric TNF, TRADD is recruited to the receptor signaling complex (H. Hsu et al., Cell 84:299–308 (1996)). TRADD can then recruit the following signal transducing molecules: 1) TRAF2, a TNFR-2- and CD40-associated molecule (M. Rothe et al., Cell 78: 681–92 (1994); M. Rothe et al., Science 269:1424–1427 (1995)), that mediates NF-kB activation, 2) RIP, originally identified as a Fas/APO-1-interacting protein by two-hybrid analysis (B. Z. Stanger et al., Cell 81: 513–23 (1995)), that mediates NF-kB activation and apoptosis (H. Hsu et al., Immunity 4: 387–396 (1996)), and 3) FADD, a Fas/APO-1- associated molecule, that mediates apoptosis (A. M. Chinnaiyan et al., Cell 81: 505–12 (1995); M. P. Boldin et al., J Biol Chem 270:7795–8 (1995); F. C. Kischkel et al., EMBO 14: 5579–5588 (1995)). Thus, the inventors demonstrate that RIP, TRAF2 and FADD could be co-immunoprecipitated with DR3. In 293 cells expressing DR3 and RIP, only a weak association could be detected between the two molecules. However, in the presence of TRADD, RIP association with DR3 was significantly enhanced. Likewise, very little TRAF2 directly co-precipitated with DR3 in 293 cells. However, when DR3 and TRAF2 were expressed in the presence of TRADD and RIP (both of which can bind TRAF2), an enhanced binding of TRAF2 to DR3 could be detected. A similar association between FADD and DR3 was also observed. In the presence of TRADD, FADD efficiently coprecipitated with DR3.

Previous studies demonstrated that FADD could recruit the ICE/CED-3-like protease FLICE to the Fas/APO-1 death inducing signaling complex (M. Muzio et al., Cell 85: 817–827 (1996); M. P. Boldin et al., Cell 85: 803–815 (1996)). To demonstrate that FLICE can associate with TNFR-1 and DR3, coprecipitation experiments in 293 cells were carried out. Interestingly, FLICE was found complexed to TNFR-1 and DR3. Co-transfection of TRADD and/or FADD failed to enhance the FLICE-TNFR-1/DR3 interaction, suggesting that endogenous amounts of these adapter molecules were sufficient to maintain this association.

EXAMPLE 6

DR3 Induced Apoptosis and NF-kB Activation

Overexpression of Fas/APO-1 and TNFR-1 in mammalian cells mimics receptor activation (M. Muzio et al., Cell 85: 817–827 (1996); M. P. Boldin et al., Cell 85: 803–815 (1996)). Thus, this system was utilized to study the functional role of DDCR. Ectopic expression of DR3 in MCF7 breast carcinoma cells and 293 human embryonic kidney cells induced rapid apoptosis.

Experimental Design

Cell death assays were performed essentially as previously described (A. M. Chinnaiyan et al., Cell 81: 505–12 (1995); M. P. Boldin et al., J Biol Chem 270: 7795-8 (1995); F. C. Kischkel et al., EMBO 14: 5579–5588 (1995); A. M. Chinnaiyan et al., J Biol Chem 271: 49614965 (1996)). Briefly, MCF-7 human breast carcinoma clonal cell lines stably transfected with either vector alone, a CrmA expression construct (M. Tewari et al., J Biol Chem 270: 3255–60 (1995)), or FADD-DN expression construct (A. M. Chinnaiyan et al., J Biol Chem 271: 49614965 (1996)) were transiently transfected with pCMV-β-galatosidase in the presence of a ten-fold excess of pcDNA3 expression constructs encoding the indicated proteins using lipofectamine (GIBCO-BRL). 293 cells were likewise transfected using the $CaPO_4$ method. The ICE family inhibitor z-VAD-fink (Enzyme Systems Products, Dublin, Calif.) was added to the cells at a concentration of 10 $\mu$M, S hrs after transfection. 32 hours following transfection, cells were fixed and stained with X-Gal as previously described (A. M. Chinnaiyan et al., Cell 81: 505–12 (1995); M. P. Boldin et al., J Biol Chem 270: 7795–8 (1995); F. C. Kischkel et al., EMBO 14: 5579–5588 (1995)). The data (mean +/– SD) shown are the percentage of round blue cells among the total number of blue cells counted. Data were obtained from at least three independent experiments.

NF-kB luciferase assays were performed as described elsewhere (H. Hsu et al., Immunity 4: 387–396 (1996); M. D. Adams et al., Nature 377. 3-174 (1995); G. S. Feng et al., J Biol Chem 271: 12129–32 (1996); M. Rothe et al., Cell 78: 681–92 (1994); M. Rothe et al., Science 269:1424–1427 (1995); A. M. Chinnaiyan et al., J Biol Chem 271: 49614965 (1996)). Briefly, 293 cells were co-transfected by calcium phosphate precipitation with pCMV-β-galactosidase, E-selectin-luciferase reporter gene (M. Rothe et al., Cell 78: 681–92 (1994); M. Rothe et al., Science 269:1424–1427 (1995)), the indicated death receptors, and the indicated dominant negative inhibitors. In addition, DR3 or DDR3 was cotransfected with the pLantern expression construct (GIBCO-BRL) which encodes green fluorescent protein (photographic inset). Cells were visualized by fluorescence microscopy using a FITC range barrier filter cube. Nuclei of transfected cells were visualized by DAPI staining and the image overlaid. (Cell death assays were performed essentially as previously described (Chinnaiyan et al., Cell 81:505–12 (1995); Boldin, et al, J. Biol. Chem. 270:7795–8 (1995); Kischkel et al, EMBO 14:5579–5588 (1995)); Chinnaiyan et al., J. Biol. Chem. 271:4961–4965 (1996)). The dominant negative inhibitors were used at a 4-fold higher quantity than the death receptors. Total DNA was kept constant.

To show that DR3 induces NF-kB activation which is inhibitable by RIP-DN (Stanger et al., Cell 81:513–23 (1995)) and TRAF2-DN (Hsu et al., Cell 81:495–504 (1995); Rothe et al., Cell 78:681–92 (1994); Rothe et al. Science 269:1424–1427 (1995)), 293 cells were co-transfected with the indicated molecules and an NF-kB luciferase reporter plasmid (Rothe et al., *Cell* 78:681–92 (1994); Rothe et al., *Science* 269:1424–1427 (1995)), and luciferase activities subsequently determined. NF-κB luciferase assays were performed as described elsewhere (Hsu et al., *Immunity* 4:387–396 (1996); Adams et al., *Nature* 377:3–174 (1995); Feng et al., *J. Biol. Chem.* 271:12129–32 (1996); Rothe et al., *Cell* 78:681–92 (1994); Rothe et al. *Science* 269:1424–1427 (1995); Chinnaiyan et al., *J. Biol. Chem.* 271:4961–4965 (1996)). Briefly, 293 cells were co-transfected by calcium phosphate precipitation with pCMB-β-galactosidase, E-selectin-luciferase reporter gene (Rothe et al., *Cell* 78:681–92 (1994); Rothe et al., *Science* 269:1424–1427 (1995)), the indicated dominant negative inhibitors. The dominant negative inhibitors were used at a 4-fold higher quantity than the death receptors. Total DNA was kept constant. Representative experiment performed in duplicate three independent times (mean±SD).

Results

The cells displayed morphological alterations typical of cells undergoing apoptosis, becoming rounded, condensed and detaching from the dish. In MCF7 cells, plasmids encoding full-length DR3 or DDR3 were co-transfected with the pLantern reporter construct encoding green fluorescent protein. Nuclei of cells transfected with DR3, but not DDR3, exhibited apoptotic morphology as assessed by DAPI staining. Similar to TNFR-1 and Fas/APO-1 (M. Muzio et al, *Cell* 85: 817–827 (1996); M. P. Boldin et al., *Cell* 85: 803–815 (1996); M. Tewari et al., *J Biol Chem* 270: 3255–60 (1995)), DR3-induced apoptosis was blocked by the inhibitors of ICE-like proteases, CrmA and z-VAD-fmk. Importantly, apoptosis induced by DR3 was also blocked by dominant negative versions of FADD (FADD-DN) or FLICE (FLICE-DN/MACHa1C360S), which were previously shown to inhibit death signaling by Fas/APO-1 and TNFR-1 (M. Muzio et al., *Cell* 85: 817–827 (1996); M. P. Boldin et al., *Cell* 85: 803–815 (1996); H. Hsu et al., *Cell* 84: 299–398 (1996); A. M. Chinnaiyan et al., *J Biol Chem* 271: 4961–4965 (1996)). Thus, FADD and the ICE-like protease FLICE are likely necessary components of DR3-induced apoptosis.

As DR3 activation recruits three molecules implicated in TNF-induced NF-kB activation, we examined whether DR3 could activate NF-kB. Transfection of a control vector or expression of Fas/APO-1 failed to induce NF-kB activation. By contrast, NF-kB was activated by ectopic expression of DR3 or TNFR-1, but not by the inactive signaling mutants DDR3 or DTNFR-1. Importantly, DR3-induced NF-kB activation was blocked by dominant negative derivatives of RIP (RIP-DN) and TRAF2 (TRAF2-DN), which were previously shown to abrogate TNF-induced NF-kB activation (H. Hsu et al., *Cell* 84: 299–398 (1996); H. Hsu et al., *Immunity* 4. 387–396 (1996)). As expected, FADD-DN did not interfere with DR3-mediated NF-kB activation (H. Hsu et al., *Cell* 84: 299–398 (1996); A. M. Chinnaiyan et al., *J Biol Chem* 271: 4961–4965 (1996)).

Thus, the experiments set forth in Examples 6 and 7 demonstrate that DR3 is a death domain-containing molecule capable of triggering both apoptosis and NF-kB activation, two pathways dominant in the regulation of the immune system. The experiments also demonstrate the internal signal transduction machinery of this novel cell death receptor. The DR3 signaling complex assembles in a hierarchical manner with the recruitment of the multivalent adapter molecule TRADD, from which two distinct signaling cascades emanate: 1) NF-kB activation mediated by TRAF2 and RIP and 2) cell death mediated by FADD, FLICE, and RIP.

It will be clear that the invention may be practiced otherwise than as particularly described in the foregoing description and examples.

Numerous modifications and variations of the present invention are possible in light of the above teachings and, therefore, are within the scope of the appended claims.

The entire disclosures of all patents, patent applications, and publications referred to herein are hereby incorporated by reference.

What is claimed is:

1. An isolated protein comprising amino acids 30 to 215 of SEQ ID NO:2.

2. The isolated protein of claim 1, which comprises amino acids 1 to 215 of SEQ ID NO:2.

3. The isolated protein of claim 1, which is produced by a recombinant host cell.

4. The isolated protein of claim 1, which comprises a heterologous polypeptide.

5. A composition comprising the isolated protein of claim 1 and a pharmaceutically acceptable carrier.

6. An isolated protein comprising the mature amino acid sequence encoded by the cDNA clone contained in ATCC Deposit No. 97456.

7. The isolated protein of claim 6, which comprises the complete amino acid sequence encoded by the cDNA clone contained in ATCC Deposit No. 97456.

8. The isolated protein of claim 6, which is produced by a recombinant host cell.

9. The isolated protein of claim 6, which comprises a heterologous polypeptide.

10. A composition comprising the isolated protein of claim 6 and a pharmaceutically acceptable carrier.

11. An isolated protein comprising 4, contiguous amino acids of a polypeptide having the amino acid sequence from 350 to 420 of SEQ ID NO:2.

12. The isolated protein of claim 1, which comprises 50 contiguous amino acids of a polypeptide having the amino acid sequence from 350 to 420 of SEQ ID NO:2.

13. The isolated protein of claim 12, which comprises amino acids 350 to 420 of SEQ ID NO:2.

14. The isolated protein of claim 11, which is produced by a recombinant host cell.

15. The isolated protein of claim 11, which comprises a heterologous polypeptide.

16. A composition comprising the isolated protein of claim 11, and a pharmaceutically acceptable carrier.

* * * * *

UNITED STATES PATENT AND TRADEMARK OFFICE
CERTIFICATE OF CORRECTION

PATENT NO. : 6,759,513 B2  Page 1 of 1
DATED : July 6, 2004
INVENTOR(S) : Yu et al.

It is certified that error appears in the above-identified patent and that said Letters Patent is hereby corrected as shown below:

Column 62,
Line 65, replace "comprising 4," with -- comprising 30 --.

Signed and Sealed this

Sixteenth Day of November, 2004

JON W. DUDAS
*Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 1783 base pairs
      (B) TYPE: nucleic acid
      (C) STRANDEDNESS: double
      (D) TOPOLOGY: both (ii) MOLECULE TYPE: cDNA (ix) FEATURE:
      (A) NAME/KEY: CDS
      (B) LOCATION: 198..1481

(xi) SEQUENCE DESCRIPTION: SEQ ID NO:1:

```
CATGGGTGGG GGTGGGGGCG CTGCTGGATT CCTGCTCTGG TGGAGGGGAA ACTTGTGAGG      60

GGCTGGTAAG CGCCCCCTCC GAAGCCTGGT GTGTGCGCGG GGGGAAGGAA GTTAGTTTCC     120

TCTCCACCCA TGGGCACCCC TTCTGCCCGG GGCCTGGGAA GTGGGCTGCT CTGTGGGCAA     180
```

```
ATGCTGGGGC CTCTGAA ATG GAG GAG ACG CAG CAG GGA GAG GCC CCA CGT        230
                   Met Glu Glu Thr Gln Gln Gly Glu Ala Pro Arg
                    1               5                  10

GGG CAG CTG CGC GGA GAG TCA GCA GCA CCT GTC CCC CAG GCG CTC CTC        278
Gly Gln Leu Arg Gly Glu Ser Ala Ala Pro Val Pro Gln Ala Leu Leu
             15                  20                  25

CTG GTG CTG CTG GGG GCC CGG GCC CAG GGC GGC ACT CGT AGC CCC AGG        326
Leu Val Leu Leu Gly Ala Arg Ala Gln Gly Gly Thr Arg Ser Pro Arg
             30                  35                  40

TGT GAC TGT GCC GGT GAC TTC CAC AAG AAG ATT GGT CTG TTT TGT TGC        374
Cys Asp Cys Ala Gly Asp Phe His Lys Lys Ile Gly Leu Phe Cys Cys
         45                  50                  55

AGA GGC TGC CCA GCG GGG CAC TAC CTG AAG GCC CCT TGC ACG GAG CCC        422
Arg Gly Cys Pro Ala Gly His Tyr Leu Lys Ala Pro Cys Thr Glu Pro
 60                  65                  70                  75

TGC GGC AAC TCC ACC TGC CTT GTG TGT CCC CAA GAC ACC TTC TTG GCC        470
Cys Gly Asn Ser Thr Cys Leu Val Cys Pro Gln Asp Thr Phe Leu Ala
                 80                  85                  90

TGG GAG AAC CAC CAT AAT TCT GAA TGT GCC CGC TGC CAG GCC TGT GAT        518
Trp Glu Asn His His Asn Ser Glu Cys Ala Arg Cys Gln Ala Cys Asp
             95                 100                 105

GAG CAG GCC TCC CAG GTG GCG CTG GAG AAC TGT TCA GCA GTG GCC GAC        566
Glu Gln Ala Ser Gln Val Ala Leu Glu Asn Cys Ser Ala Val Ala Asp
            110                 115                 120

ACC CGC TGT GGC TGT AAG CCA GGC TGG TTT GTG GAG TGC CAG GTC AGC        614
Thr Arg Cys Gly Cys Lys Pro Gly Trp Phe Val Glu Cys Gln Val Ser
        125                 130                 135

CAA TGT GTC AGC AGT TCA CCC TTC TAC TGC CAA CCA TGC CTA GAC TGC        662
Gln Cys Val Ser Ser Ser Pro Phe Tyr Cys Gln Pro Cys Leu Asp Cys
140                 145                 150                 155

GGG GCC CTG CAC CGC CAC ACA CGG CTA CTC TGT TCC CGC AGA GAT ACT        710
Gly Ala Leu His Arg His Thr Arg Leu Leu Cys Ser Arg Arg Asp Thr
                160                 165                 170

GAC TGT GGG ACC TGC CTG CCT GGC TTC TAT GAA CAT GGC GAT GGC TGC        758
Asp Cys Gly Thr Cys Leu Pro Gly Phe Tyr Glu His Gly Asp Gly Cys
            175                 180                 185

GTG TCC TGC CCC ACG AGC ACC CTG GGG AGC TGT CCA GAG CGC TGT GCC        806
Val Ser Cys Pro Thr Ser Thr Leu Gly Ser Cys Pro Glu Arg Cys Ala
            190                 195                 200

GCT GTC TGT GGC TGG AGG CAG ATG TTC TGG GTC CAG GTG CTC CTG GCT        854
Ala Val Cys Gly Trp Arg Gln Met Phe Trp Val Gln Val Leu Leu Ala
        205                 210                 215

GGC CTT GTG GTC CCC CTC CTG CTT GGG GCC ACC CTG ACC TAC ACA TAC        902
Gly Leu Val Val Pro Leu Leu Leu Gly Ala Thr Leu Thr Tyr Thr Tyr
220                 225                 230                 235

CGC CAC TGC TGG CCT CAC AAG CCC CTG GTT ACT GCA GAT GAA GCT GGG        950
Arg His Cys Trp Pro His Lys Pro Leu Val Thr Ala Asp Glu Ala Gly
                240                 245                 250

ATG GAG GCT CTG ACC CCA CCA CCG GCC ACC CAT CTG TCA CCC TTG GAC        998
Met Glu Ala Leu Thr Pro Pro Pro Ala Thr His Leu Ser Pro Leu Asp
            255                 260                 265

AGC GCC CAC ACC CTT CTA GCA CCT CCT GAC AGC AGT GAG AAG ATC TGC       1046
Ser Ala His Thr Leu Leu Ala Pro Pro Asp Ser Ser Glu Lys Ile Cys
            270                 275                 280

ACC GTC CAG TTG GTG GGT AAC AGC TGG ACC CCT GGC TAC CCC GAG ACC       1094
Thr Val Gln Leu Val Gly Asn Ser Trp Thr Pro Gly Tyr Pro Glu Thr
        285                 290                 295

CAG GAG GCG CTC TGC CCG CAG GTG ACA TGG TCC TGG GAC CAG TTG CCC       1142
Gln Glu Ala Leu Cys Pro Gln Val Thr Trp Ser Trp Asp Gln Leu Pro
```

-continued

```
                300                 305                 310                 315

AGC AGA GCT CTT GGC CCC GCT GCT GCG CCC ACA CTC TCG CCA GAG TCC        1190
Ser Arg Ala Leu Gly Pro Ala Ala Ala Pro Thr Leu Ser Pro Glu Ser
                    320                 325                 330

CCA GCC GGC TCG CCA GCC ATG ATG CTG CAG CCG GGC CCG CAG CTC TAC        1238
Pro Ala Gly Ser Pro Ala Met Met Leu Gln Pro Gly Pro Gln Leu Tyr
                335                 340                 345

GAC GTG ATG GAC GCG GTC CCA GCG CGG CGC TGG AAG GAG TTC GTG CGC        1286
Asp Val Met Asp Ala Val Pro Ala Arg Arg Trp Lys Glu Phe Val Arg
            350                 355                 360

ACG CTG GGG CTG CGC GAG GCA GAG ATC GAA GCC GTG GAG GTG GAG ATC        1334
Thr Leu Gly Leu Arg Glu Ala Glu Ile Glu Ala Val Glu Val Glu Ile
        365                 370                 375

GGC CGC TTC CGA GAC CAG CAG TAC GAG ATG CTC AAG CGC TGG CGC CAG        1382
Gly Arg Phe Arg Asp Gln Gln Tyr Glu Met Leu Lys Arg Trp Arg Gln
380                 385                 390                 395

CAG CAG CCC GCG GGC CTC GGA GCC GTT TAC GCG GCC CTG GAG CGC ATG        1430
Gln Gln Pro Ala Gly Leu Gly Ala Val Tyr Ala Ala Leu Glu Arg Met
                    400                 405                 410

GGG CTG GAC GGC TGC GTG GAA GAC TTG CGC AGC CGC CTG CAG CGC GGC        1478
Gly Leu Asp Gly Cys Val Glu Asp Leu Arg Ser Arg Leu Gln Arg Gly
                415                 420                 425

CCG TGACACGGCG CCCACTTGCC ACCTAGGCGC TCTGGTGGCC CTTGCAGAAG             1531
Pro

CCCTAAGTAC GGTTACTTAT GCGTGTAGAC ATTTTATGTC ACTTATTAAG CCGCTGGCAC     1591

GGCCCTGCGT AGCAGCACCA GCCGGCCCCA CCCCTGCTCG CCCCTATCGC TCCAGCCAAG     1651

GCGAAGAAGC ACGAACGAAT GTCGAGAGGG GGTGAAGACA TTTCTCAACT TCTCGGCCGG     1711

AGTTTGGCTG AGATCGCGGT ATTAAATCTG TGAAAGAAAA CAAAACAAAA CAAAAAAAAA     1771

AAAAAAAAAA AA                                                        1783

(2) INFORMATION FOR SEQ ID NO:2:

(i) SEQUENCE CHARACTERISTICS:
        (A) LENGTH: 428 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Glu Thr Gln Gln Gly Glu Ala Pro Arg Gly Gln Leu Arg Gly
 1               5                  10                  15

Glu Ser Ala Ala Pro Val Pro Gln Ala Leu Leu Val Leu Leu Gly
             20                  25                  30

Ala Arg Ala Gln Gly Gly Thr Arg Ser Pro Arg Cys Asp Cys Ala Gly
         35                  40                  45

Asp Phe His Lys Lys Ile Gly Leu Phe Cys Cys Arg Gly Cys Pro Ala
     50                  55                  60

Gly His Tyr Leu Lys Ala Pro Cys Thr Glu Pro Cys Gly Asn Ser Thr
 65                  70                  75                  80

Cys Leu Val Cys Pro Gln Asp Thr Phe Leu Ala Trp Glu Asn His His
                 85                  90                  95

Asn Ser Glu Cys Ala Arg Cys Gln Ala Cys Asp Glu Gln Ala Ser Gln
             100                 105                 110

Val Ala Leu Glu Asn Cys Ser Ala Val Ala Asp Thr Arg Cys Gly Cys
         115                 120                 125
```

-continued

```
Lys Pro Gly Trp Phe Val Glu Cys Gln Val Ser Gln Cys Val Ser Ser
130                 135                 140
Ser Pro Phe Tyr Cys Gln Pro Cys Leu Asp Cys Gly Ala Leu His Arg
145                 150                 155                 160
His Thr Arg Leu Leu Cys Ser Arg Arg Asp Thr Asp Cys Gly Thr Cys
                165                 170                 175
Leu Pro Gly Phe Tyr Glu His Gly Asp Gly Cys Val Ser Cys Pro Thr
            180                 185                 190
Ser Thr Leu Gly Ser Cys Pro Glu Arg Cys Ala Ala Val Cys Gly Trp
        195                 200                 205
Arg Gln Met Phe Trp Val Gln Val Leu Leu Ala Gly Leu Val Val Pro
210                 215                 220
Leu Leu Leu Gly Ala Thr Leu Thr Tyr Thr Tyr Arg His Cys Trp Pro
225                 230                 235                 240
His Lys Pro Leu Val Thr Ala Asp Glu Ala Gly Met Glu Ala Leu Thr
                245                 250                 255
Pro Pro Pro Ala Thr His Leu Ser Pro Leu Asp Ser Ala His Thr Leu
            260                 265                 270
Leu Ala Pro Pro Asp Ser Ser Glu Lys Ile Cys Thr Val Gln Leu Val
        275                 280                 285
Gly Asn Ser Trp Thr Pro Gly Tyr Pro Glu Thr Gln Glu Ala Leu Cys
290                 295                 300
Pro Gln Val Thr Trp Ser Trp Asp Gln Leu Pro Ser Arg Ala Leu Gly
305                 310                 315                 320
Pro Ala Ala Ala Pro Thr Leu Ser Pro Glu Ser Pro Ala Gly Ser Pro
                325                 330                 335
Ala Met Met Leu Gln Pro Gly Pro Gln Leu Tyr Asp Val Met Asp Ala
            340                 345                 350
Val Pro Ala Arg Arg Trp Lys Glu Phe Val Arg Thr Leu Gly Leu Arg
        355                 360                 365
Glu Ala Glu Ile Glu Ala Val Glu Val Glu Ile Gly Arg Phe Arg Asp
370                 375                 380
Gln Gln Tyr Glu Met Leu Lys Arg Trp Arg Gln Gln Pro Ala Gly
385                 390                 395                 400
Leu Gly Ala Val Tyr Ala Ala Leu Glu Arg Met Gly Leu Asp Gly Cys
                405                 410                 415
Val Glu Asp Leu Arg Ser Arg Leu Gln Arg Gly Pro
            420                 425
```

(2) INFORMATION FOR SEQ ID NO:3:

(i) SEQUENCE CHARACTERISTICS:
        (A) LENGTH: 1254 base pairs
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 1..1251

(xi) SEQUENCE DESCRIPTION: SEQ ID NO:3:

```
ATG GAG CAG CGG CCG CGG GGC TGC GCG GCG GTG GCG GCG GCG CTC CTC      48
Met Glu Gln Arg Pro Arg Gly Cys Ala Ala Val Ala Ala Ala Leu Leu
430                 435                 440

CTG GTG CTG CTG GGG GCC CGG GCC CAG GGC GGC ACT CGT AGC CCC AGG      96
```

```
                                                       -continued

Leu Val Leu Leu Gly Ala Arg Ala Gln Gly Gly Thr Arg Ser Pro Arg
445                 450                 455                 460

TGT GAC TGT GCC GGT GAC TTC CAC AAG AAG ATT GGT CTG TTT TGT TGC    144
Cys Asp Cys Ala Gly Asp Phe His Lys Lys Ile Gly Leu Phe Cys Cys
                        465                 470                 475

AGA GGC TGC CCA GCG GGG CAC TAC CTG AAG GCC CCT TGC ACG GAG CCC    192
Arg Gly Cys Pro Ala Gly His Tyr Leu Lys Ala Pro Cys Thr Glu Pro
                480                 485                 490

TGC GGC AAC TCC ACC TGC CTT GTG TGT CCC CAA GAC ACC TTC TTG GCC    240
Cys Gly Asn Ser Thr Cys Leu Val Cys Pro Gln Asp Thr Phe Leu Ala
            495                 500                 505

TGG GAG AAC CAC CAT AAT TCT GAA TGT GCC CGC TGC CAG GCC TGT GAT    288
Trp Glu Asn His His Asn Ser Glu Cys Ala Arg Cys Gln Ala Cys Asp
        510                 515                 520

GAG CAG GCC TCC CAG GTG GCG CTG GAG AAC TGT TCA GCA GTG GCC GAC    336
Glu Gln Ala Ser Gln Val Ala Leu Glu Asn Cys Ser Ala Val Ala Asp
525                 530                 535                 540

ACC CGC TGT GGC TGT AAG CCA GGC TGG TTT GTG GAG TGC CAG GTC AGC    384
Thr Arg Cys Gly Cys Lys Pro Gly Trp Phe Val Glu Cys Gln Val Ser
                        545                 550                 555

CAA TGT GTC AGC AGT TCA CCC TTC TAC TGC CAA CCA TGC CTA GAC TGC    432
Gln Cys Val Ser Ser Ser Pro Phe Tyr Cys Gln Pro Cys Leu Asp Cys
                560                 565                 570

GGG GCC CTG CAC CGC CAC ACA CGG CTA CTC TGT TCC CGC AGA GAT ACT    480
Gly Ala Leu His Arg His Thr Arg Leu Leu Cys Ser Arg Arg Asp Thr
            575                 580                 585

GAC TGT GGG ACC TGC CTG CCT GGC TTC TAT GAA CAT GGC GAT GGC TGC    528
Asp Cys Gly Thr Cys Leu Pro Gly Phe Tyr Glu His Gly Asp Gly Cys
        590                 595                 600

GTG TCC TGC CCC ACG AGC ACC CTG GGG AGC TGT CCA GAG CGC TGT GCC    576
Val Ser Cys Pro Thr Ser Thr Leu Gly Ser Cys Pro Glu Arg Cys Ala
605                 610                 615                 620

GCT GTC TGT GGC TGG AGG CAG ATG TTC TGG GTC CAG GTG CTC CTG GCT    624
Ala Val Cys Gly Trp Arg Gln Met Phe Trp Val Gln Val Leu Leu Ala
                        625                 630                 635

GGC CTT GTG GTC CCC CTC CTG CTT GGG GCC ACC CTG ACC TAC ACA TAC    672
Gly Leu Val Val Pro Leu Leu Leu Gly Ala Thr Leu Thr Tyr Thr Tyr
                640                 645                 650

CGC CAC TGC TGG CCT CAC AAG CCC CTG GTT ACT GCA GAT GAA GCT GGG    720
Arg His Cys Trp Pro His Lys Pro Leu Val Thr Ala Asp Glu Ala Gly
            655                 660                 665

ATG GAG GCT CTG ACC CCA CCG CCG GCC ACC CAT CTG TCA CCC TTG GAC    768
Met Glu Ala Leu Thr Pro Pro Pro Ala Thr His Leu Ser Pro Leu Asp
        670                 675                 680

AGC GCC CAC ACC CTT CTA GCA CCT CCT GAC AGC AGT GAG AAG ATC TGC    816
Ser Ala His Thr Leu Leu Ala Pro Pro Asp Ser Ser Glu Lys Ile Cys
685                 690                 695                 700

ACC GTC CAG TTG GTG GGT AAC AGC TGG ACC CCT GGC TAC CCC GAG ACC    864
Thr Val Gln Leu Val Gly Asn Ser Trp Thr Pro Gly Tyr Pro Glu Thr
                        705                 710                 715

CAG GAG GCG CTC TGC CCG CAG GTG ACA TGG TCC TGG GAC CAG TTG CCC    912
Gln Glu Ala Leu Cys Pro Gln Val Thr Trp Ser Trp Asp Gln Leu Pro
                720                 725                 730

AGC AGA GCT CTT GGC CCC GCT GCT GCG CCC ACA CTC TCG CCA GAG TCC    960
Ser Arg Ala Leu Gly Pro Ala Ala Ala Pro Thr Leu Ser Pro Glu Ser
            735                 740                 745

CCA GCC GGC TCG CCA GCC ATG ATG CTG CAG CCG GGC CCG CAG CTC TAC    1008
Pro Ala Gly Ser Pro Ala Met Met Leu Gln Pro Gly Pro Gln Leu Tyr
        750                 755                 760
```

-continued

```
GAC GTG ATG GAC GCG GTC CCA GCG CGG CGC TGG AAG GAG TTC GTG CGC      1056
Asp Val Met Asp Ala Val Pro Ala Arg Arg Trp Lys Glu Phe Val Arg
765             770             775             780

ACG CTG GGG CTG CGC GAG GCA GAG ATC GAA GCC GTG GAG GTG GAG ATC      1104
Thr Leu Gly Leu Arg Glu Ala Glu Ile Glu Ala Val Glu Val Glu Ile
            785             790             795

GGC CGC TTC CGA GAC CAG CAG TAC GAG ATG CTC AAG CGC TGG CGC CAG      1152
Gly Arg Phe Arg Asp Gln Gln Tyr Glu Met Leu Lys Arg Trp Arg Gln
        800             805             810

CAG CAG CCC GCG GGC CTC GGA GCC GTT TAC GCG GCC CTG GAG CGC ATG      1200
Gln Gln Pro Ala Gly Leu Gly Ala Val Tyr Ala Ala Leu Glu Arg Met
    815             820             825

GGG CTG GAC GGC TGC GTG GAA GAC TTG CGC AGC CGC CTG CAG CGC GGC      1248
Gly Leu Asp Gly Cys Val Glu Asp Leu Arg Ser Arg Leu Gln Arg Gly
830             835             840

CCG TGA                                                              1254
Pro
845
```

(2) INFORMATION FOR SEQ ID NO:4:

(i) SEQUENCE CHARACTERISTICS:
        (A) LENGTH: 417 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Gln Arg Pro Arg Gly Cys Ala Ala Val Ala Ala Leu Leu
1               5                   10                  15

Leu Val Leu Leu Gly Ala Arg Ala Gln Gly Gly Thr Arg Ser Pro Arg
                20                  25                  30

Cys Asp Cys Ala Gly Asp Phe His Lys Lys Ile Gly Leu Phe Cys Cys
            35                  40                  45

Arg Gly Cys Pro Ala Gly His Tyr Leu Lys Ala Pro Cys Thr Glu Pro
        50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
        195                 200                 205

Gly Leu Val Val Pro Leu Leu Leu Gly Ala Thr Leu Thr Tyr Thr Tyr
    210                 215                 220

Arg His Cys Trp Pro His Lys Pro Leu Val Thr Ala Asp Glu Ala Gly
```

-continued

```
            225                 230                 235                 240

Met Glu Ala Leu Thr Pro Pro Ala Thr His Leu Ser Pro Leu Asp
                    245                 250                 255

Ser Ala His Thr Leu Leu Ala Pro Pro Asp Ser Ser Glu Lys Ile Cys
                    260                 265                 270

Thr Val Gln Leu Val Gly Asn Ser Trp Thr Pro Gly Tyr Pro Glu Thr
                    275                 280                 285

Gln Glu Ala Leu Cys Pro Gln Val Thr Trp Ser Trp Asp Gln Leu Pro
        290                 295                 300

Ser Arg Ala Leu Gly Pro Ala Ala Pro Thr Leu Ser Pro Glu Ser
305                 310                 315                 320

Pro Ala Gly Ser Pro Ala Met Met Leu Gln Pro Gly Pro Gln Leu Tyr
                    325                 330                 335

Asp Val Met Asp Ala Val Pro Ala Arg Arg Trp Lys Glu Phe Val Arg
                    340                 345                 350

Thr Leu Gly Leu Arg Glu Ala Glu Ile Glu Ala Val Glu Val Glu Ile
                    355                 360                 365

Gly Arg Phe Arg Asp Gln Gln Tyr Glu Met Leu Lys Arg Trp Arg Gln
        370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                    405                 410                 415

Pro
```

(2) INFORMATION FOR SEQ ID NO:5:

(i) SEQUENCE CHARACTERISTICS:
        (A) LENGTH: 455 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:5:

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160
```

-continued

```
Lys Gln Asn Thr Val Cys Thr Cys His Ala Gly Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455
```

(2) INFORMATION FOR SEQ ID NO:6:

(i) SEQUENCE CHARACTERISTICS:
        (A) LENGTH: 335 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:6:

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45
```

-continued

```
Leu Glu Gly Leu His His Asp Gly Gln Phe Cys His Lys Pro Cys Pro
 50                  55                  60

Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
                 85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Gln Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335
```

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCGCCATGGG GGCCCGGCGG CAG                                                23

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCGAAGCTTC TAGGACCCAG AACATCTGCC                           30

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CGCGGATCCG CCATCATGGA GGAGACGCAG CAG                       33

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CGCGGATCCG CCATCATGGA GCAGCGGCCG CGG                       33

(2) INFORMATION FOR SEQ ID NO:11:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCGTCTAGAT CAAAGCGTAG TCTGGGACGT CGTATGGGTA CGGGCCGCGC TGCA    54

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CGCGGATCCG CCATCATGGA GGAGACGCAG CAG                       33

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
                                                        -continued

CGCGGATCCG CCATCATGGA GCAGCGGCCG CGG                         33

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CGCGGATCCT CACGGGCCGC GCTGCA                                 26

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CGCGGATCCG CCATCATGGA GGAGACGCAG CAG                         33

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CGCGGATCCG CCATCATGGA GCAGCGGCCG CGG                         33

(2) INFORMATION FOR SEQ ID NO:17:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GCGAGATCTA GTCTGGACCC AGAACATCTG CCTCC                       35
```